United States Patent [19]
Arita et al.

[11] Patent Number: 5,750,768
[45] Date of Patent: May 12, 1998

[54] METHOD OF MANUFACTURING α-OXOCARBOXYLATE AND CATALYST ADOPTED IN THE METHOD

[75] Inventors: Yoshitaka Arita; Akihiko Ohta; Ren Hasebe, all of Suita; Noboru Saito, Takatsuki, all of Japan

[73] Assignee: Nippon Shokubai Co., Ltd., Osaka, Japan

[21] Appl. No.: 689,274

[22] Filed: Aug. 6, 1996

[30] Foreign Application Priority Data

Aug. 24, 1995 [JP] Japan ................... 7-216379
Jul. 5, 1996 [JP] Japan ................... 8-176810

[51] Int. Cl.$^6$ ................................................ C07C 69/66
[52] U.S. Cl. ................................................ 560/177
[58] Field of Search ................................................ 560/177

[56] References Cited

U.S. PATENT DOCUMENTS 5,118,652  6/1992  Anantaneni et al. ............ 502/213

FOREIGN PATENT DOCUMENTS

| | | |
|---|---|---|
| 149439 A2 | 7/1985 | European Pat. Off. . |
| 0 354 894 A1 | 2/1990 | European Pat. Off. . |
| 57-176929 A | 10/1982 | Japan . |
| 58-059933 A | 4/1983 | Japan . |
| 63-295528 A | 12/1988 | Japan . |
| 3-63245 A | 3/1991 | Japan . |
| 3-232835 A | 10/1991 | Japan . |
| 4-66856 B2 | 10/1992 | Japan . |
| 6-321866 A | 11/1994 | Japan . |
| 7-501854 A | 2/1995 | Japan . |
| 7-51567 A | 2/1995 | Japan . |
| 8-34762 A | 2/1996 | Japan . |

*Primary Examiner*—Gary Geist
*Assistant Examiner*—Rosalynd A. Keys
*Attorney, Agent, or Firm*—Kubovcik & Kubovcik

[57] ABSTRACT

A method of manufacturing α-oxocarboxylate includes the steps of: (i) carrying out a vapor phase oxidation of 1,2-diol of formula (1) in a primary reaction vessel, (ii) introducing a resulting gaseous α-oxoaldehyde and/or α-hydroxyaldehyde in a secondary reaction vessel together with alcohol or olefin which is converted into a gas form in a vaporizing chamber, and (iii) carrying out an oxidative esterification of the gaseous α-oxoaldehyde and/or α-hydroxyaldehyde molecular oxygen in a presence of inorganic oxide containing phosphorus as a catalyst in the secondary reaction vessel.

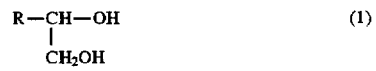

(R is a hydrogen atom or an organic residue).

The described method permits α-oxocarboxylate to be manufactured economically and effectively in practically one step using inexpensive 1,2-diol such as ethylene glycol or propylene glycol.

35 Claims, 1 Drawing Sheet

METHOD OF MANUFACTURING α-OXOCARBOXYLATE AND CATALYST ADOPTED IN THE METHOD

FIELD OF THE INVENTION

The present invention relates to a method of manufacturing α-oxocarboxylate by a vapor phase reaction and also relates to a catalyst adopted in the method.

Glyoxylate as a typical example of α-oxocarboxylate is an industrially useful compound. For example, sodium polyacetal carboxylate obtained from a polymer of glyoxylate is a useful compound as a builder such as a detergent builder of a detergent composition, etc. For example, glyoxylic acid obtained by a hydrolysis of glyoxylate is a very useful compound especially for intermediate materials of various products such as medical products, cosmetics, perfumes, agricultural chemicals, etc.

BACKGROUND OF THE INVENTION

Conventionally, various composite methods have been proposed as a method of manufacturing glyoxylate as a typical example of α-oxocarboxylate. Such composite methods include:

(1) A method of carrying out a dehydrogenation of glycolate by vapor phase oxidation;

(2) A method of carrying out of an esterification of glyoxylic acid by using alcohol; and (3) A method of ozonizing fumarate and subsequently reducing ozonized fumarate with hydrogen (Japanese Laid-Open Patent Application No. 321866/1994 (Tokukaihei 6-321866).

The method (1) is known, for example, through U.S. Pat. No. 5,118,652 wherein iron phosphate is used as a catalyst and Japanese Laid-Open Patent Application No. 152442/1985 (Tokukaisho 60-152442) wherein metallic Ag is used as a catalyst. In this method, glycolate used as a raw material is typically obtained by a liquid phase oxidation of ethylene glycol using a noble metal catalyst such as platinum, etc., to obtain glycolic acid and subsequently carrying out an esterification of the resulting glycolic acid with alcohol in the presence of an acidic catalyst.

However, the described method (1) requires the process of separating glycolate from unreacted alcohol. Therefore, although the method which adopts iron phosphate as a catalyst offers a high yield of a target product based on glycolate (around 80 percent), a total percentage yield of glyoxylate (target product) based on ethylene glycol (raw material) remains in the order of sixties. Besides, the described method requires complicated processes and a long time, and an overall cost for devices becomes high.

On the other hand, in the latter example of adopting metallic Ag as a catalyst, although a reaction can be performed in high concentration and at high space velocity, a conversion is low, and a percentage yield remains in the order of forties. Therefore, when adopting the method, a large amount of unreacted glycolate is needed to be collected and reutilized, and glyoxylate cannot be obtained efficiently. Therefore, a total yield of the glyoxylate (target product) based on ethylene glycol (raw material) becomes still lower. Besides, the method requires a complicated process and a long time, and a high cost would be required for the devices for use in the method.

According to the method (2), normally, hemiacetal of glyoxylate is obtained as a main component, and a target product of glyoxylate is hardly obtained. Therefore, a method of isolating glyoxylate by a thermal decomposition of hemiacetal has been proposed in Japanese Laid-Open Patent Application No. 176929/1982 (Tokukaisho 57-176929). According to the method, however, both yield and purity are low, and glyoxylate cannot be obtained efficiently at low cost. To prevent the described problem, another method has been proposed. That is, the method which permits glyoxylate to be obtained from glyoxylic acid in one step by suppressing a generation of hemiacetal is disclosed in Japanese Laid-Open Patent Application No. 66856/1992 (Tokukaihei 4-66856).

Moreover, the method (2) has the following problems. Glyoxylate to be adopted as raw material in the method (2) is obtained by a method using an aqueous solution of glyoxal as a raw material. However, as the method disclosed in Japanese Laid-Open Patent Application No. 63245/1991 (Tokukaihei 3-63245) requires a liquid phase reaction under acidic conditions, various restrictions are posed in terms of materials for the devices used in the method. On the other hand, the method of Japanese Laid-Open Patent Application No. 51567/1995 (Tokukaihei 7-51567) offers an insufficient percentage yield (in the order of fifties). Another method is disclosed in Japanese Laid-Open Patent Application No. 501854/1995 (Tokukaihei 7-501854) wherein glyoxylate is obtained almost quantitatively by an electrochemical reduction of oxalic acid. However, this method requires an expensive electrode reaction vessel. A still another method of obtaining glyoxylate is disclosed in Japanese Laid-Open Patent Application No. 295528/1988 (Tokukaisho 63-295528) wherein glyoxylate is obtained by ozonizing maleic acid and subsequently reducing the resulting ozonized maleic acid with hydrogen. However, this method also has a drawback that expensive devices including an ozone generating device, etc., are needed. Besides, oxalic acid and maleic acid adopted as raw materials of glyoxylic acid are both expensive.

As described, the above-listed methods all require high cost, and complicated processes and a long time to complete the reaction. As this also increases a cost incurred for the devices used in each method, glyoxylate cannot be manufactured at low cost.

On the other hand, the method (3) enables glyoxylate to be obtained at a high percentage yield (in the order of eighties). However, the method (3) requires variable reaction vessels such as an ozone generating device, etc., and also requires a long time to complete the reaction. Thus, the method (3) fails to manufacture glyoxylate at low cost.

As described, the conventional methods of manufacturing α-oxocarboxylate have various drawbacks in terms of productivity, cost, etc., and do not enable α-oxocarboxylate to be manufactured efficiently at low cost.

SUMMARY OF THE INVENTION

The present invention is achieved in the hope of finding a method of solving the above-discussed and numerous other disadvantages and deficiencies of the prior art, and accordingly, objects of the present invention are to provide a method of manufacturing α-oxocarboxylate economically and efficiently and to provide a catalyst suited for use in the method.

Extensive studies have been made by the inventors of the present invention to achieve a new method of manufacturing α-oxocarboxylate, to fulfill the above-mentioned object, and the inventors of the present invention have found that α-oxocarboxylate can be manufactured economically and efficiently by carrying out a vapor phase oxidization of α-oxoaldehyde and/or α-hydroxyaldehyde and alcohol or olefin in the presence of oxygen and a catalyst. They have also found that α-oxocarboxylate can be manufactured at still improved efficiency by adopting a catalyst including inorganic oxide containing phosphorus to complete the present invention.

Specifically, the above-mentioned object is achieved by the method of manufacturing α-oxocarboxylate in accordance with the present invention which includes the step of performing a vapor phase oxidation reaction of α-oxoaldehyde and/or α-hydroxyaldehyde with alcohol or olefin in the presence of oxygen and a catalyst. The method permits α-oxocarboxylate to be manufactured economically and efficiently.

It is preferable that the described method further includes the step of:

producing gaseous α-oxoaldehyde of formula (2) and/or α-hydroxyaldehyde of formula (3) obtained by carrying out a vapor phase oxidation of 1,2-diol of formula (1) prior to the process of carrying out the vapor phase oxidation reaction of α-oxoaldehyde and/or α-hydroxyaldehyde and alcohol or olefin.

(R is a hydrogen atom or an organic residue).

(R is a hydrogen atom or an organic residue).

(R is a hydrogen atom or an organic residue).

In the described method of the present invention, inexpensive 1,2-diol is used, and a vapor phase oxidation of 1,2-diol and a vapor phase reaction of α-oxoaldehyde and/or α-hydroxyaldehyde and alcohol or olefin are carried out continuously, thereby permitting the α-oxocarboxylate to be manufactured practically in one step. Therefore, the method of the present invention permits α-oxocarboxylate to be manufactured economically and efficiently.

The described method may further include the step of generating α-oxoaldehyde and/or α-hydroxyaldehyde by heating a solution of α-oxoaldehyde and/or a solution of α-hydroxyaldehyde prior to carrying out a vapor phase oxidation of α-oxoaldehyde and/or α-hydroxyaldehyde and alcohol or olefin. This method permits α-oxocarboxylate to be manufactured economically and effectively using a solution of α-oxoaldehyde and/or a solution of α-hydroxyaldehyde.

It is also preferable that the described method further includes the step of adding a component containing phosphorus to the 1,2-diol prior to performing the vapor phase oxidation of 1,2-diol in such an amount that a concentration of phosphorus with respect to the 1,2-diol is not less than 20 ppm, prior to carrying out the vapor phase oxidation of α-oxoaldehyde and/or α-hydroxyaldehyde and alcohol or olefin in the presence of oxygen and the catalyst and that the vapor phase oxidation of α-oxoaldehyde and/or α-hydroxyaldehyde and alcohol or olefin is carried out in the presence of metallic silver. As a result, gaseous α-oxoaldehyde and/or α-hydroxyaldehyde can be supplied more efficiently, as this permits the α-oxocarboxylate to be manufactured at an improved efficiency.

With regard to the described method, it is more preferable that the catalyst includes an inorganic oxide containing phosphorus. It is further preferable that the inorganic oxide containing phosphorus is composed of metal phosphate or heteropolyacid containing phosphorus. It is still more preferable that the catalyst is a mixture of metal phosphate and inorganic oxide, as this permits α-oxocarboxylate to be manufactured at a still improved efficiency.

In the described method, by adopting glyoxal as α-oxoaldehyde, and glycol aldehyde as α-hydroxyaldehyde, glyoxylate can be manufactured efficiently.

In order to achieve the aforementioned objects, the catalyst to be adopted in the method of the present invention is characterized by including inorganic oxide containing phosphorus.

For a fuller understanding of the nature and advantages of the invention, reference should be made to the ensuing detailed description taken in conjunction with the accompanying drawing.

DESCRIPTION OF THE EMBODIMENTS

Figure 1:
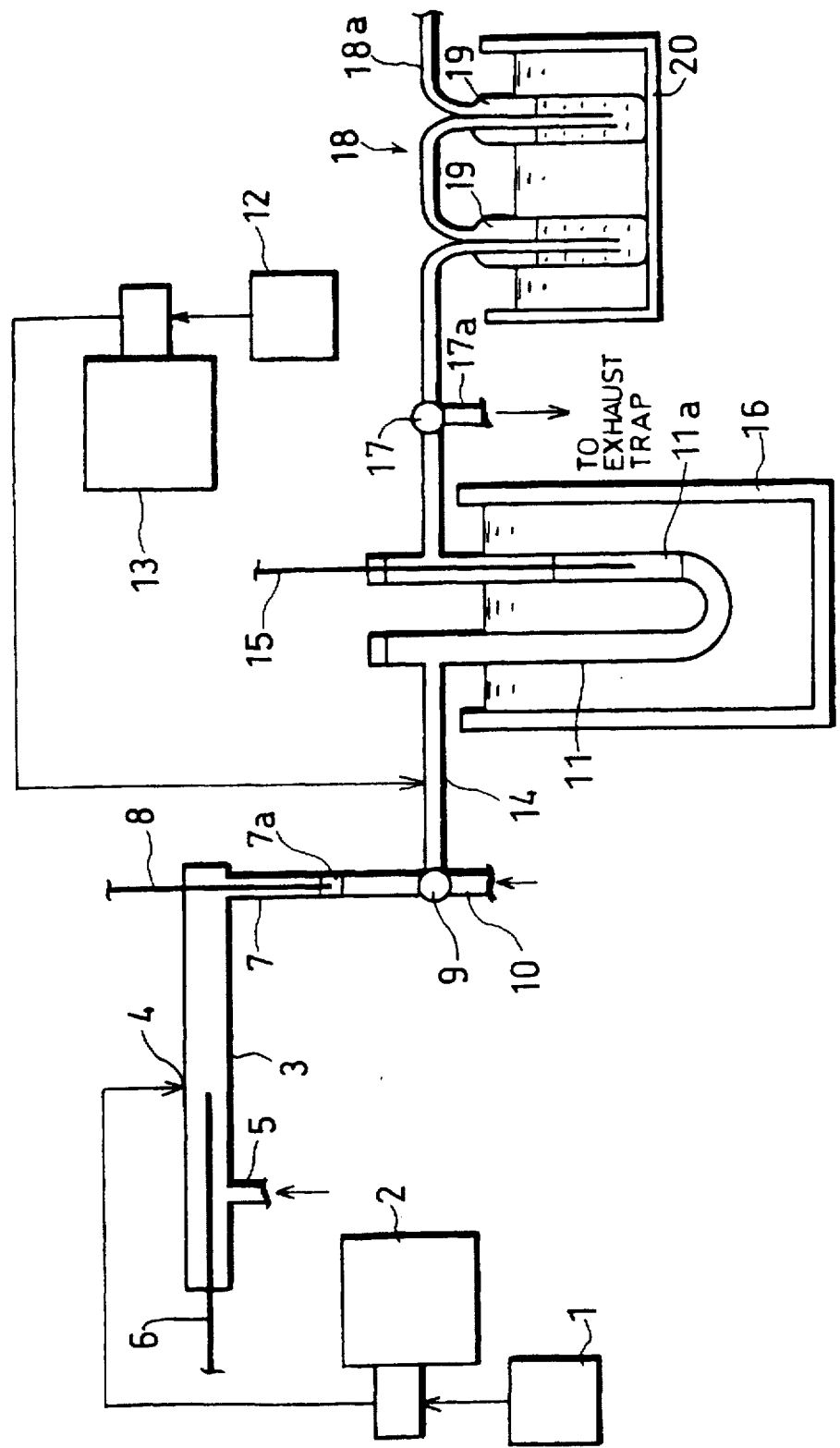
FIG. 1 is a block diagram showing a schematic structure of a reaction vessel which is suited for use in the method of manufacturing α-oxocarboxylate in accordance with one embodiment of the present invention.

The following descriptions will describe the present invention in detail.

A method of manufacturing α-oxocarboxylate of the present invention includes the step of carrying out a vapor phase oxidation of α-oxoaldehyde and/or α-hydroxyaldehyde and alcohol or olefin in the presence of oxygen and a catalyst, i.e., an oxidative esterification of α-oxoaldehyde and/or α-hydroxyaldehyde.

For the gaseous α-oxoaldehyde and/or α-hydroxyaldehyde, α-oxoaldehyde and/or gaseous α-hydroxyaldehyde obtained by a vapor phase oxidation of 1,2-diol (hereinafter simply referred to as 1,2-diol) represented by the formula (1) or by heating a solution of α-oxoaldehyde and/or a solution of α-hydroxyaldehyde may be adopted.

(R is a hydrogen atom or an organic residue).

In the described method, by adopting gaseous α-oxoaldehyde of the formula (2) obtained by a vapor phase oxidization of 1,2-diol and/or gaseous α-hydroxyaldehyde of the formula (3), the gas resulting from the vapor phase oxidation of 1,2-diol can be esterified by oxidation in the vapor phase. Namely, as the described method permits different vapor phase reactions to be combined, a subsequent reaction of a reaction intermediate of gaseous α-oxoaldehyde (2) and/or α-hydroxyaldehyde (3) can be continued without taking them out of the reaction system, thereby permitting α-oxocarboxylate to be manufactured from 1,2-diol practically in one step.

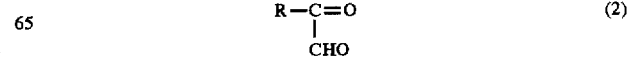

(R is a hydrogen atom or an organic residue),

(R is a hydrogen atom or an organic residue).

The described α-oxoaldehyde (2) is a compound wherein a substituent represented by R is a hydrogen atom or an organic residue in the formula (2). Examples of such α-oxoaldehyde (2) include: glyoxal (with a substituent represented by R of a hydrogen atom); α-oxoaldehyde with a substituent represented by R of a saturated aliphatic hydrocarbon group with 1 to 4 carbon atoms, such as pyruvic aldehyde, 2-oxobutanal, 2-oxopentanal, 2-oxohexanal, 3-methyl-2-oxobutanal, 3-methyl-2-oxopentanal, 4-methyl-2-oxopentanal, etc.; α-oxoaldehyde with a substituent represented by R of an unsaturated aliphatic hydrocarbon group of 2 to 3 carbon atoms such as 2-oxo-3-butenal, 2-oxo-4-pentenal, 2-oxo-3-pentenal; oxoaldehyde with a substituent represented by R of an aromatic hydrocarbon group such as 2-phenyl-2-oxoethanal, etc.

The described α-hydroxyaldehyde (3) is a compound wherein a substituent represented by R is a hydrogen atom or an organic residue in the formula (3). Examples of such α-hydroxyaldehyde (3) include: glycol aldehyde (with a substituent represented by R of a hydrogen atom); α-hydroxyaldehyde with a substituent represented by R of a saturated aliphatic hydrocarbon group with 1 to 4 carbon atoms, such as 2-hydroxypropanal, 2-hydroxybutanal, 2-hydroxypentanal, 2-hydroxyhexanal, 3-methyl-2-hydroxybutanal, 3-methyl-2-hydroxypentanal, 4-methyl-2-hydroxypentanal, etc.; α-hydroxyaldehyde with a substituent represented by R of an unsaturated aliphatic hydrocarbon group with 2 to 3 carbon atoms such as 2-hydroxy-3-butenal, 2-hydroxy-4-pentenal, 2-hydroxy-3-pentenal; hydroxyaldehyde with a substituent represented by R of an aromatic hydrocarbon group such as 2-phenyl-2-hydroxyethanal, etc.

The described 1,2-diol used as a raw material in the primary reaction is a compound with a substituent represented by R of a hydrogen atom or an organic residue in the formula (1). Such 1,2-diol is not particularly limited as long as it can be vaporized under atmospheric conditions. Examples of such 1,2-diol include ethylene glycol (with a substituent represented by R of a hydrogen atom); 1,2-diol (with a substituent represented by R of a saturated aliphatic hydrocarbon group with 1 to 4 carbon atoms) such as propylene glycol, 1,2-butanediol, 1,2-pentanediol, 1,2-hexanediol, 3-methyl-1,2-butanediol, 4-methyl-1,2-pentanediol, 3-methyl-1,2-pentanediol, etc.; 1,2-diol (with a substituent represented by R of an unsaturated aliphatic hydrocarbon group with 2 to 3 carbon atoms) such as 1,2-dihydroxy-3-butene, 1,2-dihydroxy-4-pentene, 1,2-dihydroxy-3-pentene; 1,2-dihydroxy-3-pentene, etc.; 1,2-diol (with a substituent represented by R of an aromatic hydrocarbon group) such as 1-phenyl-1,2-dihydroxyethane, etc.

The method of performing a vapor phase oxidation of 1,2-diol (hereinafter referred as a primary reaction) is not particularly limited as long as gaseous α-oxoaldehyde (2) and/or α-hydroxyaldehyde (3) can be obtained. Namely, the primary reaction can be performed by a known method of manufacturing α-oxoaldehyde (2) or α-hydroxyaldehyde (3).

For example, as a typical method of manufacturing glyoxal representing α-oxoaldehyde (2), a method of performing a vapor phase oxidization of ethylene glycol in the presence of metallic Ag, CuO—ZnO/α—Al$_2$O$_3$, Ag$_2$O—SiO$_2$—ZnO, etc., as a catalyst is known. Especially, when a reaction is performed using metallic Ag in the presence of a small amount of phosphorus, glyoxal is obtained at high yield (at maximum yield of 84 percent) (Japanese Laid-Open Patent Application No. 59933/1983 (Tokukaisho 58-59933) and Japanese Laid-Open Patent Application No. 232835/1991 (Tokukaihei 3-232835).

Specifically, for a reaction vessel to be used in the primary reaction, a fixed bed flow reactor having a two-level structure of the primary reaction vessel and a secondary reaction vessel (to be described later) may be adopted. Specifically, the primary reaction may be performed in the following manner: The first level of the primary reaction vessel is filled with, for example, a commercially available metallic Ag having a uniform particle diameter as a catalyst and gaseous 1,2-diol and oxygen are fed therein. Then, the resulting gas is introduced in the secondary reaction vessel for use in carrying out the secondary level of the reaction to be described later. Gaseous 1,2-diol to be supplied to the primary reaction vessel is obtained, for example, by heating 1,2-diol in a liquid form at a temperature in a range of 150° to 300° C. in a vaporizing chamber that is connected to the primary reaction vessel.

The oxygen used in the primary reaction can be supplied using gas containing molecular oxygen. For the gas containing molecular oxygen used in the primary reaction, gas containing normal molecular oxygen such as oxygen, gas, mixed gas obtained by diluting oxygen, air, etc., with an inactive gas such as nitrogen, helium, etc., may be used. However, it is industrially preferable to adopt air or a mixed gas of air and inactive gas.

The composition of the gas to be supplied to the primary reaction is selected to have a ratio of 1,2-diol/oxygen of 4~10/4~10 (vol. percent) and a rest of the composition is selected to be nitrogen gas (hereinafter referred as a nitrogen balance). Such composition may include water in a range of not more than 34 vol. percent if necessary. Here, water may be added in a range of not more than 50 percent by weight to 1,2-diol in a liquid form before being vaporized. However, it should be noted here that when water is added to 1,2-diol in the liquid form before being vaporized, the content of water in the gas supplied for use in the secondary section increases, and this may cause the yield of the target product of α-oxocarboxylate to be lowered. Therefore, it is preferable not to add water. If it is necessary to add water, the amount of water should be reduced to the minimum.

In the case of adopting the metallic silver as the catalyst for the primary reaction, a component including phosphorus such as triethyl phosphite, diethyl phosphate, etc., may be added to a raw material of 1,2-diol if necessary. Such component containing phosphorus is preferably added in an amount such that an amount of phosphorus to be added with respect to 1,2-diol (concentration) is not less than 20 ppm, more preferably in a range of 40 to 100 ppm, still more preferably in a range of 50 to 70 ppm. By adding the component containing phosphorus in the described range, an amount of α-oxoaldehyde (2) produced can be still increased.

Additionally, the primary reaction is typically performed at a space velocity (SV) in a range of 10,000 to 1,000,000 hr$^{-1}$. The reaction temperature of the primary reaction may be selected in a range of 400° to 600° C. according to the composition of the gas supplied. When the primary reaction is performed in the fixed bed flow reactor filled with metallic Ag as a catalyst under a gas supply, space velocity and reaction temperature respectively in the described ranges, the following results are obtained:

The conversion of 1,2-diol . . . 80 to 100 percent

The yield of α-oxoaldehyde (2) ... 40 to 85 percent
The yield of α-hydroxyaldehyde (3) ... 0 to 25 percent.

On the other hand, gaseous α-oxoaldehyde or α-hydroxyaldehyde is obtained by heating a solution of α-oxoaldehyde or a solution of α-hydroxyaldehyde instead of carrying out the primary reaction, for example, by heating a mixed solution in which alcohol is added in to be converted into a gaseous form, or by heating the solution of α-oxoaldehyde or the solution of α-hydroxyaldehyde to be converted into a gaseous form while feeding gaseous olefin. For the solution of α-hydroxyaldehyde, for example, an aqueous solution of glyoxal may be used. For the solution of α-hydroxyaldehyde, a solution of a dimer of α-hydroxyaldehyde such as a solution obtained by dissolving a dimer of glycolaldehyde in water and methanol may be adopted. It should be noted here that when a solution of α-oxoaldehyde or a solution of α-hydroxyaldehyde is used as a reaction solution, if it contains a large amount of water, the yield of the α-oxocarboxylate (target product) will be lowered. For this reason, the higher the concentration of the solution, the more preferable it is.

For a reaction vessel for use in an oxidative esterification reaction of gaseous α-oxoaldehyde and/or α-hydroxyaldehyde (hereinafter referred to as a secondary reaction), a fixed bed flow reactor may be used.

With regard to alcohol or olefin used in the reaction, examples of alcohol include: alkyl alcohol having 1 ~18 carbon atoms that is industrially available with ease, such as methanol, ethanol, 1-propanol, 2-propanol, 1-butanol, 2-butanol, iso-butanol, tert-butanol, hexanol, cyclohexanol, octanol, 2-ethylhexanol, lauryl alcohol, stearyl alcohol, etc.; aromatic alcohol such as phenol, benzyl alcohol, etc. Among the above-listed examples, alkyl alcohol having 1 to 4 carbon atoms such as methanol, ethanol, 1-propanol, 2-propanol, 1-butanol, 2-butanol, isobutanol, tert-butanol are preferable, and methanol, is more preferable. On the other hand, examples of olefin include those having 2 to 4 carbon atoms such as ethylene, propylene, 1-butene, 2-butene, isobutene, etc.

A molar ratio of the total amount of α-oxoaldehyde and α-hydroxyaldehyde to alcohol or olefin used in the secondary reaction is theoretically in unity. The ratio in amount of the sum of α-oxoaldehyde and α-hydroxyaldehyde to oxygen is not particularly limited. The ratio in amount of α-oxoaldehyde to α-hydroxyaldehyde to be supplied for the secondary reaction is not particularly limited, and it is also permitted to use only either one of them.

In the secondary reaction, oxygen can be supplied using the aforementioned gas containing molecular oxygen. The preferable composition of the gas to be supplied to the secondary reaction is as follows: sum of α-oxoaldehyde and α-hydroxyaldehyde:oxygen:alcohol or olefin:water=3 to 5:3 to 8:10 to 25:an amount produced by the primary reaction (vol. percent, nitrogen balance). If alcohol or olefin is used in an amount less than the described range, the yield of α-oxocarboxylate will be lowered. On the other hand, if alcohol or olefin is used in an amount greater than the described range, the yield of the α-oxocarboxylate will not be improved, and an amount of unreacted alcohol or olefin will be increased on the contrary. Namely, the amount of alcohol or olefin to be collected for reutilization will be increased. For this reason, it is unpreferable to use alcohol or olefin in a greater amount than the described range.

The reaction temperature of the secondary reaction can be selected at random according to a catalyst used in the reaction. However, the reaction temperature is typically in a range of 150° to 500° C., preferably in a range of 180° to 400° C. Additionally, the space velocity (SV) may be selected as desired to be suited for the catalyst employed. However, the space velocity is typically in a range of 500 to 10,000 hr$^{-1}$, preferably in a range of 1,000 to 5,000 hr$^{-1}$.

For the catalyst of the secondary reaction, a catalyst including inorganic oxide containing phosphorus is preferable. Such inorganic oxide containing phosphorus is not particularly limited, and various types of inorganic oxide containing phosphorus are applicable to the secondary reaction of the present invention. However, metal phosphate, and heteropolyacid containing phosphorus are preferable.

The kinds of metal of metal phosphate are not limited as long as phosphate can be produced. Examples of such metal include: alkali earth metal, B, Al, Ti, V, Cr, Mn, Fe, Co, Ni, Zn, Zr, Mo, Pd, Ag, Cd, Sn, Pb, etc. The ratio of metal to phosphorus of the metal of metal phosphate can be deviated from the theoretical ratio in quantity of orthophosphate. Specifically, the ratio of metal: phosphorus may be in a range of 1/0.5:1/2. However, it is preferable to approximate the ratio to the theoretical ratio in amount of orthophosphate. Only one kind of the above-listed metal phosphate may be adopted, or two or more kinds thereof may be suitably mixed and adopted. Specifically, the metal phosphate including two or more kinds of metals may be used. Additionally, such metal phosphate may be a mixture including at least two kinds of metal phosphate containing mutually different metals.

Namely, the metal phosphate in accordance with the present invention includes metal phosphate including one kind of metal, metal phosphate including two or more kinds of metals, a mixture obtained by mixing two or more kinds of metal phosphate including mutually different metals, and a mixture of the above.

When the reaction vessel is filled with metal phosphate as a catalyst layer, different metal phosphate may be adopted between a gas introducing side and a gas discharge side.

For the metal phosphate, a commercially available reagent may be used without applying thereto any treatment, or may be prepared by a coprecipitation method from a solution or a kneading method in a slurry form using a metallic salt and phosphate. Examples of such metallic salt include nitrate, carbonate, oxalate, hydroxide, chloride, and the like. Examples of phosphoric acid source include: phosphate such as orthophosphate, ammonium phosphate, ammonium hydrogenphosphate, ammonium dihydrogen phosphate, and the like. A combination of the metallic salt and phosphoric acid source is not particularly limited, and various combinations thereof are applicable.

The metal phosphate may be used as a catalyst without having applied thereto any treatment. However, it is preferable to use the metal phosphate after drying it in an air at a temperature in a range of 100° to 120° C., and is calcined in the air. If necessary, it is preferable that the resulting metal phosphate is molded, or the particle diameter thereof is aligned. The calcination temperature varies according to the kind of the metal phosphate. However, the calcination temperature is typically in a range of 300° to 700° C., more preferably in a range of 400° to 600° C.

The metal phosphate may be used alone as a catalyst. However, it is preferable to use the metal phosphate in combination with an inorganic oxide. Examples of inorganic oxide include: silica, titania, zirconia, niobium oxide, diatomaceous earth, and the like. For the titanium, both anatase type and rutile type may be used.

An amount of inorganic oxide to be mixed in the metal phosphate varies depending of the kind of metal phosphate. However, it is preferably used in an amount of 1 to 90 percent by weight, more preferably, 1 to 60 percent by weight with respect to the total amount of metal phosphate and the inorganic oxide.

The heteropolyacid containing phosphorus is not particularly limited. However, Keggin type heteropolyacid of the formula $H_aPM_{12}O_{40} \cdot nH_2O$ is preferable because of its function as a catalyst (wherein M is at least one element selected from the group consisting of tungsten, molybdenum and vanadium, a is a value determined by M, and n is 0 or a positive integer).

The heteropolyacid containing phosphorus may be a heteropolyacid salt of formula $H_{a-b}M'_bPM_{12}O_{40} \cdot nH_2O$ that being a compound obtained by a part or all of H in the Keggin type heteropolyacid is substituted with metal such as alkali metal, alkali earth metal, transition metal, etc., (wherein M is an element of at least one kind selected from the group consisting of tungsten, molybdenum and vanadium, M' is a metal element such as an alkali metal, alkali earth metal, transition metal, etc., a is a numerical value determined by M, b is a numerical value selected at random from the range of $0<b \leq a$, and n is 0 or a positive integer).

The heteropolyacid or heteropolyacid salt may be used as a catalyst without applying thereto any treatment. However, it is preferable to use it by supporting it on a support material. For the support material, those which are stable against heteropolyacid and heteropolyacid salt and do not have adverse effects on the secondary reaction are preferable. Examples of such heteropolyacid or heteropolyacid salt include: silica, titanium, diatomaceous earth, etc. The method of supporting heteropolyacid or heteropolyacid salt on the support material are not particularly limited, and a so-called kneading method, or the impregnating supporting method may be adopted. The heteropolyacid containing phosphorus is not needed to be dried or calcined prior to the secondary reaction; however, it is preferable to dry or calcine at higher temperature than the reaction temperature.

The following will explain one modification of the present invention in reference to FIG. 1. The explanations will be given through the case where the fixed bed flow reactor of a two-linked level structure as a reaction vessel, and alcohol are used. It should be noted here that the reaction vessel suited for use in the present invention is not limited to the reaction vessel shown in FIG. 1.

As shown in FIG. 1, the reaction vessel used in this modification includes a raw material tank 1, a vaporizing chamber 3, a primary reaction vessel 7, a raw material tank 12, a vaporizing chamber 14, a secondary reaction vessel 11, etc.

In the raw material tank 1, a raw material in a liquid form prepared by adding triethyl phosphite as a phosphorus source for accelerating the reaction and/or water to 1,2-diol (hereinafter simply referred to as a primary reaction raw material) is poured. The primary reaction raw material in the raw material tank 1 is supplied quantitatively to the vaporizing chamber 3 by a pump 2 such as a micro pump, etc.

In the vaporizing chamber 3, formed are a raw material supply opening 4 for supplying therethrough the primary reaction raw material from the raw material tank 1 through the pump 2 and a gas supply opening 5 for supplying therethrough a mixed gas of air and nitrogen. The vaporizing chamber 3 has a sheathed heater wound therearound for heating the primary reaction raw material to be vaporized. In the vaporizing chamber 3, mounted is a protection tube for thermocouple with a diameter of 1/16 inch (not shown) for controlling the temperature in the vaporization chamber 3, and in the protection tube, a thermocouple 6 with a diameter of 0.5 mm is inserted. The vaporizing chamber 3 has an opening that is connected to the primary reaction vessel 7, and vaporized primary reaction raw material is supplied to the primary reaction vessel 7 together with the mixed gas.

The primary reaction vessel 7 is prepared by introducing quartz wool as a holder of the catalyst in a reaction vessel made of SUS (Stainless Steel) with a diameter of 1/4 inch and a predetermined amount of metallic Ag (for example, available from Yokohama Metal Co., Ltd.) to fill the reaction tube therewith. Further, a catalyst layer 7a made of metallic Ag is formed for feeding air. The primary reaction vessel 7 has a sheathed heater wound therearound for heating the catalyst layer 7a. Further, a protection tube for thermocouple (not shown) with a diameter of 1/16 inch (not shown) is mounted in the primary reaction vessel 7 for measuring and controlling the temperature of the catalyst layer 7a as in the vaporizing chamber 3. In the protection tube, a thermocouple 8 with a diameter of 0.5 mm is inserted. The primary reaction vessel 7 has a gas discharge opening connected to a three-way cock 9.

The three-way cock 9 is provided for mixing a reactant gas including α-oxoaldehyde (2) and/or α-hydroxyaldehyde (3) supplied from the primary reaction vessel 7 with oxygen or air supplied through the gas supply opening 10 and supplying the resulting mixed gas to the vaporizing chamber 14. When the composition of the reactant gas resulting from the primary reaction is to be analyzed, the three-way cock 9 is switched to discharge the reactant gas through the gas supply opening 10. The reactant gas is collected into water, for example, in a gas collecting bottle (not shown) connected to the gas supply opening 10, that is cooled in an ice bath.

In the raw material tank 12, placed is alcohol. The alcohol in the raw material tank 12 is quantitatively supplied to the vaporizing chamber 14 by a pump 13 such as a micro-pump, etc.

To the vaporizing chamber 14, supplied is the reactant gas from the primary reaction and oxygen or nitrogen are supplied through the three-way cock 9, and alcohol in a liquid form is supplied from the raw material tank 12 through the pump 13. The vaporizing chamber 14 has a sheathed heater wound therearound which is heated to a predetermined temperature to vaporize alcohol. The discharge opening of the vaporizing chamber 14 is connected to the secondary reaction vessel 11. The gas and the vaporized alcohol supplied from the three-way cock 9 are mixed, and the resulting mixed gas is supplied to the secondary reaction vessel 11.

The secondary reaction vessel 11 is a U-shape reaction vessel made of SUS with an inner diameter of 10 mm in which a predetermined amount of catalyst (hereinafter referred to as a secondary reaction catalyst) for use in the secondary reaction is placed. Further, a catalyst layer 11a made of the secondary reaction catalyst is formed for allowing gas to feed. The secondary reaction vessel 11 can be heated in a molten salt bath 16. Further, a protection tube for thermocouple (not shown) with a diameter of 1/16 inch (not shown) is mounted in the secondary reaction vessel 11 for measuring and controlling the temperature of the catalyst layer 11a. In the protection tube, a thermocouple 15 with a diameter of 0.5 mm is inserted. The secondary reaction vessel 11 has a gas opening connected to a gas collecting unit 18 for collecting gas resulting from the secondary reaction through a three-way cock 17. Namely, the reactant gas resulting from the secondary reaction is collected by the gas collecting unit 18. For example, when the reactant gas is not collected, the three-way cock 17 is switched to discharge the reactant gas to the discharge trap (not shown) through the discharge opening 17a.

The gas collecting unit 18 includes gas collecting bottles 19 connected in series and an ice bath 20 for cooling the gas collecting bottles 19. In the gas collecting bottles 19, solvent which permits the reactant gas to be absorbed, such as acetonitrile, etc., is placed, and the reactant gas is cooled to a freezing point and is collected. The gas collecting unit 18 has a gas discharge opening 18a connected to a discharge trap (not shown).

Next, an example method of manufacturing α-oxocarboxylate using the reaction vessel having the described arrangement will be explained.

First, a mixed gas of air and nitrogen is continuously supplied to the gas supply opening 5 of the vaporization chamber 3. In the meantime, the primary raw material in a liquid form including 1,2-diol is continuously supplied to the raw material supply opening 4 of the vaporization chamber 3 through the pump 2. Then, in the vaporization chamber 3, the primary reaction raw material is vaporized by applying thereto heat at a predetermined temperature to be mixed with the above-mentioned mixed gas. Then, the resulting mixed gas is supplied to the primary reaction vessel 7.

The resulting mixed gas is fed in the catalyst layer 7a of the primary reaction vessel 7 that is heated to the predetermined temperature to carry out the primary reaction. Thereafter, the reactant gas is sent to the three-way cock 9.

Then, oxygen or air is introduced into the three-way cock 9 through the gas supply opening 10, and is mixed with the reactant gas resulting from the primary reaction to be supplied to the vaporizing chamber 14. To the vaporizing chamber 14, alcohol in a liquid form is supplied from the raw material tank 12 connected thereto through the pump 13, and the supplied alcohol is vaporized by applying thereto heat to be supplied to the secondary reaction vessel 11 together with the air or oxygen and resulting gas from the primary reaction supplied from the three-way cock 9.

Thereafter, the mixed gas supplied from the vaporizing chamber 14 is fed in the catalyst layer 11a of the secondary reaction vessel 11 that is heated to a predetermined temperature to carry out the secondary reaction. Thereafter, the reactant gas is sent to the gas collecting unit 18 through the three-way cock 17, and the reactant gas is cooled to a freezing point and is collected with acetonitrile, or the like, thereby obtaining α-oxocarboxylate.

In the case of adopting olefin in place of alcohol, the olefin may be supplied to the secondary reaction vessel 11 through the gas supply opening 10. In this arrangement, the raw material tank 12, the pump 13, the vaporizing chamber 14, etc., can be omitted.

In the case where a secondary reaction is carried out using gaseous α-oxoaldehyde and/or α-hydroxyaldehyde obtained by heating a solution of α-oxoaldehyde or α-hydroxyaldehyde instead of carrying out the primary reaction, the reaction can be performed by connecting the gas supply line to the vaporizing chamber 14 to supply the mixed gas of air and nitrogen and placing alcohol and a solution of α-oxoaldehyde or α-hydroxyaldehyde in the raw material tank 12 to be mixed therein. Or the secondary reaction may be carried out by connecting the supply line to the vaporizing chamber 14 and supplying a mixed gas of air and nitrogen, while supplying olefin to the secondary reaction vessel 11 through the gas supply opening 10 to place the solution of α-oxoaldehyde or α-hydroxyaldehyde in the raw material tank 12. In this case, respective devices for carrying out the primary reaction are omitted.

Hereinafter, this invention is illustrated by the following examples of some preferred embodiments in comparison with reference examples not according to the undermentioned examples. Furthermore, in the examples and comparative examples, the unit "part(s)" denotes "part(s) by weight".

In the undermentioned examples 1 through 40 and reference examples, conversion, selectivity and yield are calculated in the following manner. The reactant gas resulting from the primary reaction is cooled to a freezing point and is collected with water, and is analyzed using high performance liquid chromatography equipped with a differential refractometer detector. By the high performance liquid chromatography, unreacted ethylene glycol (hereinafter referred to as EG), resulting glyoxal (hereinafter referred to as GLO) and glycol aldehyde (hereinafter referred to as GAL) are determined. The reactant gas from the secondary reaction is cooled to a freezing point and is collected with acetonitrile, and is analyzed using the high speed liquid chromatography equipped with differential refractometer detector, and a gas chromatography equipped with a Frame Ionization Detector (FID). Then, by the high speed liquid chromatography, unreacted GLO and GAL are determined, and by the gas chromatography, the target product of glyoxylate (hereinafter referred to as RGO) is determined.

The reacted EG (mol)=EG supplied (mol)−unreacted EG (mol)

The conversion of EG (%)=(reacted EG (mol)/EG supplied (mol))×100

The yield GLO (%)=(GLO produced from the primary reaction (mol)/EG supplied (mol))×100

The yield GAL(%)=(GAL (mol) produced from the primary reaction (mol)/EG supplied (mol))×100

The total amount of reacted GLO and GAL (mol)=Total amount of GLO and GAL produced from the primary reaction (mol)−total amount of unreacted GLO and GAL (mol)

The total conversion of GLO and GAL (%)=(total amount of reacted GLO and GAL (mol)/total amount of GLO and GAL produced from the primary reaction (mol))×100

The selectivity of RGO (%)=(RGO (mol) produced/total amount of reacted GLO and GAL (mol))×100

The yield of RGO based on EG (%)=(RGO (mol) produced/EG supplied (mol))×100

The space velocity (SV) (hr$^{-1}$)=(amount of gas supplied (ml) per hour/amount of catalyst (ml).

Here, the space velocity is measured in the standard state.

EXAMPLE 1

A secondary reaction was performed using gaseous GLO and/or GAL resulting from the primary reaction. The primary reaction for obtaining gaseous GLO and/or GAL by oxidative dehydrogenation of EG was performed using the described reaction vessel under the following conditions. The vaporization chamber 3 was heated beforehand to 180° C. prior to supplying the primary reaction raw material and was maintained at 180° C. The amount of triethyl phosphite added with respect to EG in the primary reaction raw material was selected so as to have a concentration of phosphorus with respect to EG of 60 ppm.

The composition of the mixed gas supplied from the vaporization chamber 3 to the primary reaction vessel 7, i.e., the composition of the gas to be supplied to the primary reaction vessel 7 was selected so as to have EG of 6 vol. percent and oxygen of 7 vol. percent (nitrogen balance). As the catalyst for use in the primary reaction (hereinafter

13 referred to as a primary catalyst), 0.8 g of metallic Ag with a particle diameter in a range of 20 to 30 mesh (available from Yokohama Metal Co. Ltd.) was used. The described primary reaction was performed at a reaction temperature of 440° C. and a space velocity (SV) of 830,000 $hr^{-1}$.

The primary reaction was performed under the described conditions, and the resulting reactant gas was analyzed in the following manner. As a result, the reactant gas showed a conversion of EG of 98 percent, a yield of GLO of 82 percent and a yield of GAL of 1 percent.

The secondary reaction for obtaining the RGO was performed using the above-mentioned reaction vessel under the following conditions.

In this example, methanol was adopted as alcohol, and the composition of the gas to be supplied from the vaporizing chamber 14 to the secondary reaction vessel 11 was selected to have a total amount of GLO and GAL of 4 vol. percent, oxygen of 5 vol. percent, and methanol of 20 vol. percent (nitrogen balance) as shown in Table 1. Additional pure oxygen was added through the gas supply opening 10 only to have a sufficient amount thereof.

For the catalyst for use in the secondary reaction (hereinafter referred to as the secondary reaction catalyst), iron (III) phosphate prepared in the following manner was used. Specifically, moisture of the reagent of iron (III) phosphate ($FePO_4 \cdot 4H_2O$ available from Katayama Chemical Industries, Ltd.) was adjusted with water, and was placed in a vat made of SUS. Thereafter, the reagent was dried in the air at 120° C., and was calcined at 500° C. for three hours. Thereafter, a particle diameter thereof was adjusted to be 9 ~ 20 mesh. Then, the secondary reaction vessel 11 was filled with the secondary reaction catalyst. Here, a ratio of phosphorus to iron was 1 to 1.

The described secondary reaction was performed at a reaction temperature of 250° C., and a space velocity (SV) of 2,000 $hr^{-1}$ as shown in Table 1.

The secondary reaction was performed under the described conditions, and the resulting reactant gas was analyzed in the above-mentioned manner. As a result, as shown in Table 1, the reactant gas showed a total conversion of GLO and GAL of 100 percent, a selectivity of methyl glyoxylate (hereinafter referred to as MGO) of 74 percent, and a yield of MGO based on EG of 61 percent.

EXAMPLE 2

A primary reaction was performed under the same condition as Example 1. Therefore, the composition of the resulting reactant gas from the primary reaction was equivalent to that of Example 1.

For the secondary reaction catalyst, iron phosphate prepared by the coprecipitation method was adopted. Specifically, the iron phosphate was obtained in the following manner: A predetermined amount of iron (III) nitrate enneahydrate ($Fe(NO_3)_3 \cdot 9H_2O$ available from Wako Pure Chemical Industries, Ltd.) was dissolved in water, and a predetermined amount of 85 percent solution of phosphoric acid ($H_3PO_4$ available from Wako Pure Chemical Industries, Ltd.) was added thereto. To the solution, 28 percent ammonium solution (available from Kishida Chemical Co., Ltd.) was added dropwise to generate precipitate. This dropwise addition of the ammonium solution was stopped when the solution showed a pH of 7. The resulting precipitate was condensed into a slurry form in a hot bath, and the resulting slurry was dried and calcined and the particle diameter thereof was adjusted in the same manner as Example 1. Then, the secondary reaction vessel 11 was filled with the secondary reaction catalyst. The ratio of phosphorus to iron was 2 to 1.

14

The secondary reaction was performed by supplying the mixed gas having the same composition as that adopted in Example 1 to the secondary reaction vessel 11 filled with the reaction catalyst under the reaction conditions shown in Table 1 in the same manner as Example 1. The results obtained from this example are shown in Table 1.

EXAMPLE 3

The primary reaction was performed under the same condition as Example 1. Therefore, the composition of the resulting reactant gas from the primary reaction was equivalent to that of Example 1.

For the secondary reaction catalyst, iron phosphate prepared by the coprecipitation method was adopted. Specifically, a predetermined amount of iron (III) nitrate enneahydrate ($Fe(NO_3)_3 \cdot 9H_2O$ available from Wako Pure Chemical Industries, Ltd.) was dissolved in water, and a predetermined amount of 85 percent solution of phosphoric acid ($H_3PO_4$ available from Wako Pure Chemical Industries, Ltd.) was added. To the solution, 28 percent ammonium solution (available from Kishida Chemistry Co., Ltd.) was added dropwise to generate precipitate. This dropwise addition of ammonium solution was stopped when the solution showed a pH of 7. The resulting precipitate was condensed into a slurry form in a hot bath, and the resulting slurry was dried and calcined and the particle diameter thereof was adjusted in the same manner as Example 1. Then, the secondary reaction vessel 11 was filled with the secondary reaction catalyst. The ratio of phosphorus to iron was 0.6 to 1.

The gas supplied in the secondary reaction was obtained by adding pure oxygen and gaseous methanol to the reactant gas resulting from the primary reaction so as to have the composition of total amount of GLO and GAL of 4 vol. percent, oxygen of 5 vol. percent and methanol of 15 vol. percent (nitrogen balance) as shown in Table 1.

The secondary reaction was performed by supplying the mixed gas having the above-mentioned composition to the secondary reaction vessel 11 filled with the secondary reaction catalyst under the reaction conditions shown in Table 1 in the same manner as Example 1. The results obtained from this example are shown in Table 1.

EXAMPLE 4

The primary reaction was performed under the same condition as Example 1. Therefore, the composition of the resulting reactant gas from the primary reaction was equivalent to that of Example 1.

For the secondary reaction catalyst, iron phosphate prepared by the coprecipitation method was adopted. Specifically, a predetermined amount of iron (III) nitrate enneahydrate ($Fe(NO_3)_3 \cdot 9H_2O$ available from Wako Pure Chemical Industries, Ltd.) was dissolved in water, and a predetermined amount of 85 percent solution of phosphoric acid ($H_3PO_4$ available from Wako Pure Chemical Industries, Ltd.) was added. To the solution, 28 percent ammonium solution (available from Kishida Chemistry Co., Ltd.) was added dropwise to generate precipitate. This dropwise addition of ammonium solution was stopped when the solution showed a pH of 7. The resulting precipitate was condensed into a slurry form in a hot bath, and the resulting slurry was dried and calcined and the particle diameter thereof was adjusted in the same manner as Example 1. Then, the secondary reaction vessel 11 was filled with the secondary reaction catalyst. The ratio of phosphorus to iron was 1.4 to 1.

The gas supplied in the secondary reaction was obtained by adding pure oxygen and gaseous methanol to the reactant gas resulting from the primary reaction so as to have a composition of total amount of GLO and GAL of 4 vol. percent, oxygen of 5 vol. percent and methanol of 15 vol. percent (nitrogen balance) as shown in Table 1.

The secondary reaction was performed by supplying the mixed gas having the above-mentioned composition to the secondary reaction vessel 11 filled with the secondary reaction catalyst under the reaction conditions shown in Table 1 in the same manner as Example 1. The results obtained from this example are shown in Table 1.

EXAMPLE 5

A primary reaction was performed under the same condition as Example 1. Therefore, the composition of the resulting reactant gas from the primary reaction was equivalent to that of Example 1.

For the secondary reaction catalyst, boron phosphate prepared by the following manner was adopted. Specifically, a predetermined amount of boric acid ($H_3BO_4$ available from Wako Pure Chemical Industries, Ltd.) was dissolved in water, and a predetermined amount of 85 percent solution of phosphoric acid was added thereto to generate precipitate. The resulting precipitate was condensed into a slurry form in a hot bath at 90° C., and the resulting slurry was dried and calcined and the particle diameter thereof was adjusted in the same manner as Example 1. Then, the secondary reaction vessel 11 was filled with the secondary reaction catalyst. The ratio of phosphorus to boron was 0.8 to 1.

The secondary reaction was performed by supplying the mixed gas having the above-mentioned composition to the secondary reaction vessel 11 filled with the reaction catalyst under the reaction conditions shown in Table 1 in the same manner as Example 1. The results obtained from this example are shown in Table 1.

EXAMPLE 6

A primary reaction was performed under the same condition as Example 1. Therefore, the composition of the resulting reactant gas from the primary reaction was equivalent to that of Example 1.

For the secondary reaction catalyst, titanium phosphate prepared by the coprecipitation method was adopted. Specifically, a predetermined amount of anatase-type titanium dioxide ($TiO_2$ available from Wako Pure Chemical Industries, Ltd.) was placed in a mortar, and a predetermined amount of 85 percent solution of phosphoric acid was kneaded with water to adjust a moisture thereof. Then, the resulting product was dried, calcined and the particle diameter thereof was aligned in the same manner as Example 1. Then, the secondary reaction vessel 11 was filled with the secondary reaction catalyst. The ratio of phosphorus to titanium was 0.5 to 1.

The gas supplied in the secondary reaction was obtained by adding pure oxygen and gaseous methanol to the reactant gas resulting from the primary reaction so as to have the composition of the total amount of GLO and GAL of 4 vol. percent, oxygen of 5 vol. percent and methanol of 25 vol. percent (nitrogen balance) as shown in Table 1.

The secondary reaction was performed by supplying the mixed gas having the above-mentioned composition to the secondary reaction vessel 11 filled with the reaction catalyst under the reaction conditions shown in Table 1 in the same manner as Example 1. The results obtained from this example are shown in Table 1.

EXAMPLE 7

A primary reaction was performed under the same condition as Example 1. Therefore, the composition of the resulting reactant gas from the primary reaction was equivalent to that of Example 1.

For the secondary reaction catalyst, chromium phosphate prepared in the following manner was adopted. Specifically, a predetermined amount of chromium (III) nitrate enneahydrate ($Cr(NO_3)_3 \cdot 9H_2O$ available from Wako Pure Chemical Industries, Ltd.) was dissolved in water, and a predetermined amount of 85 percent solution of phosphoric acid was added. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of phosphorus to chromium was 1.2 to 1.

The secondary reaction was performed by supplying a mixed gas having the same composition as the mixed gas adopted in Example 1 to the secondary reaction vessel 11 filled with the secondary reaction catalyst under the reaction conditions shown in Table 1 in the same manner as Example 1. The results obtained from this example are shown in Table 1.

EXAMPLE 8

To the gas to be supplied to the primary reaction vessel 7, water was added. Namely, the composition of the gas to be supplied to the primary reaction vessel 7 was selected to have EG of 5 vol. percent, oxygen of 6 vol. percent and water of 13 vol. percent (nitrogen balance). The described primary reaction was performed in the same manner as Example 1 except that the reaction temperature and space velocity (SV) were altered to 540° C. and 830,000 $hr^{-1}$ respectively. As a result, the resulting gas showed a conversion of EG of 96 percent, a yield of GLO of 80 percent and a yield of the GAL of 1 percent.

For the secondary reaction catalyst, nickel phosphate ($Ni_{1.5}P_1$) prepared in the following manner was adopted. Specifically, first, a reagent of nickel phosphate heptahydrate ($Ni_3(PO_4)_2 \cdot 7H_2O$ available from Yoneyama Chemical Industries, Ltd.) was dissolved in water to adjust a moisture thereof. Then, the moisture controlled nickel phosphate heptahydrate was dried, calcined, and the particle diameter thereof was aligned in the same manner as Example 1. Then, the secondary reaction vessel 11 was filled with the secondary reaction catalyst. The ratio of phosphorus to nickel was 1 to 1.5.

The gas supplied in the secondary reaction was selected to have the composition of the sum of GLO and GAL of 3 vol. percent, oxygen of 4 vol. percent, water of 10 vol. percent and methanol of 18 vol. percent (nitrogen balance) as shown in Table 1.

The secondary reaction was performed by supplying the mixed gas having the above-mentioned composition to the secondary reaction vessel 11 filled with the reaction catalyst under the reaction conditions shown in Table 1 in the same manner as Example 1. The results obtained from this example are shown in Table 1.

EXAMPLE 9

A primary reaction was performed under the same condition as Example 8. Therefore, the composition of the

17 resulting reactant gas from the primary reaction was equivalent to that of Example 8.

For the secondary reaction catalyst, zirconium phosphate prepared in the following manner was adopted. Specifically, a predetermined amount of zirconyl nitrate dihydrate (ZrO($NO_3$)$_2$·$2H_2O$ available from Wako Pure Chemical Industries, Ltd.) was dissolved in water, and a predetermined amount of 85 percent solution of phosphoric acid was added. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was aligned in the same manner as Example 2. Then, the secondary reaction vessel 11 was filled with the secondary reaction catalyst. The ratio of phosphorus to zirconium was 0.8 to 1.

The secondary reaction was performed by supplying a mixed gas having the same composition as that adopted in Example 8 to the secondary reaction vessel 11 filled with the reaction catalyst under the reaction conditions shown in Table 1 in the same manner as Example 8. The results obtained from this example are shown in Table 1.

EXAMPLE 10

A primary reaction was performed under the same condition as Example 1. Therefore, the composition of the resulting reactant gas from the primary reaction was equivalent to that of Example 1.

For the secondary reaction catalyst, tin diphosphate prepared by the coprecipitation method in the following manner was adopted. Moisture of a reagent of tin pyrophosphate ($Sn_2P_2O_7$ available from Mitsuwa Chemical Industries., Ltd.) was adjusted with water, and a resulting moisture-controlled tin prophosphate was dried, calcined and the particle diameter thereof was aligned in the same manner as Example 1. Then, the secondary reaction vessel 11 was filled with the secondary reaction catalyst. The ratio of phosphorus to tin was 1 to 1.

The secondary reaction was performed by supplying a mixed gas having the composition described in Example 1. to the secondary reaction vessel 11 filled with the reaction catalyst under the reaction conditions shown in Table 1 in the same manner as Example 1. The results obtained from this example are shown in Table 1.

18

EXAMPLE 11

A primary reaction was performed under the same condition as Example 1. Therefore, the composition of the resulting reactant gas from the primary reaction was equivalent to that of Example 1.

For the secondary reaction catalyst, a catalyst prepared by the below-explained coprecipitation method was adopted. Specifically, a predetermined amount of iron (III)nitrate enneahydrate was dissolved in water, and a predetermined amount of 85 percent solution of phosphoric acid was added. To the solution, a solution obtained by dissolving ammonium metavanadate ($NH_4VO_3$ available from Kishida Chemical Co., Ltd.) in an aqueous oxalic acid solution (($COOH)_2$ available from Wako Pure Chemical Industries, Ltd.) was added as a V source. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of iron:vanadium:phosphorus was 1:0.2:1.

The secondary reaction was performed by supplying a mixed gas having the described in Example 1. composition to the secondary reaction vessel 11 filled with the reaction catalyst under the reaction conditions shown in Table 2 in the same manner as Example 1. The results obtained from this example are shown in Table 2.

EXAMPLE 12

A primary reaction was performed under the same condition as Example 1. Therefore, the composition of the resulting reactant gas from the primary reaction was equivalent to that of Example 1.

For the secondary reaction catalyst, a catalyst prepared by the coprecipitation method in the following manner was adopted. A predetermined amount of iron (III) nitrate enneahydrate and a predetermined amount of chromium (III) nitrate enneahydrate were dissolved in water, and a predetermined amount of 85 percent solution of phosphoric acid was added thereto. To the solution, 28 percent ammonium solution was added dropwise to generate precipitate. This dropwise addition of ammonium solution was stopped when

TABLE 1

| EXAMPLE | COMPOSITION OF GAS SUPPLIED (VOL %, NITROGEN BALANCE) | | | | SPACE VELOCITY SV ($hr^{-1}$) | REACTION TEMPERATURE (°C.) | CONVERSION OF GLO + GAL (%) | SELECTIVITY OF MGO | YIELD OF MGO (%) BASED ON EG |
|---|---|---|---|---|---|---|---|---|---|
|  | GLO + GAL | OXYGEN | WATER | METHANOL |  |  |  |  |  |
| 1 | 4 | 5 | — | 20 | 2,000 | 250 | 100 | 74 | 61 |
| 2 | 4 | 5 | — | 20 | 3,000 | 200 | 94 | 64 | 50 |
| 3 | 4 | 5 | — | 15 | 3,000 | 250 | 97 | 63 | 51 |
| 4 | 4 | 5 | — | 10 | 2,000 | 240 | 99 | 57 | 46 |
| 5 | 4 | 5 | — | 20 | 3,000 | 280 | 98 | 54 | 44 |
| 6 | 4 | 5 | — | 25 | 3,000 | 320 | 95 | 63 | 50 |
| 7 | 4 | 5 | — | 20 | 2,000 | 250 | 91 | 65 | 49 |
| 8 | 3 | 4 | 10 | 18 | 2,000 | 350 | 93 | 59 | 44 |
| 9 | 3 | 4 | 10 | 18 | 3,000 | 330 | 98 | 61 | 48 |
| 10 | 4 | 5 | — | 20 | 3,000 | 300 | 87 | 55 | 40 |

In table 1, EG is ethylene glycol, GLO + GAL is a total amount of glyoxal and glycol aldehyde, and MGO is methyl glyoxylic acid.

the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of iron:chromium-:phosphorus was 1:1:1.

The secondary reaction was performed by supplying mixed gas having the composition described in Example 1 to the secondary reaction vessel 11 filled with the reaction catalyst under the reaction conditions shown in Table 2 min the same manner as Example 1. The results obtained from this example are shown in Table 2.

EXAMPLE 13

A primary reaction was performed under the same condition as Example 8. Therefore, the composition of the resulting reactant gas from the primary reaction was equivalent to that of Example 8.

For the secondary reaction catalyst, a catalyst prepared by the coprecipitation method in the following manner was adopted. A predetermined amount of iron (III) nitrate enneahydrate was dissolved in water, and a predetermined amount of 85 percent solution of phosphoric acid was added thereto. To the solution, a solution obtained by dissolving a predetermined amount of palladium (II) nitrate (Pd(NO$_3$)$_2$ available from Wako Pure Chemical Industries, Ltd.) in a solution of nitrate was added as a palladium source. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of iron:palladium:phosphorus was 1:0.01:1.

The secondary reaction was performed by supplying a mixed gas having the same composition as that adopted in Example 8 to the secondary reaction vessel 11 filled with the reaction catalyst under the reaction conditions shown in Table 2 in the same manner as Example 8. The results obtained from this example are shown in Table 2.

EXAMPLE 14

A primary reaction was performed under the same condition as Example 1. Therefore, the composition of the resulting reactant gas from the primary reaction was equivalent to that of Example 1.

For the secondary reaction catalyst, a catalyst prepared by the below-explained coprecipitation method was adopted. Specifically, a predetermined amount of iron (III) nitrate enneahydrate and a predetermined amount of silver nitrate (AgNO$_3$ available from Wako Pure Chemical Industries, Ltd.) were dissolved in water, and a predetermined amount of 85 percent solution of phosphoric acid was added. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of iron:silver:phosphorus was 1:0.8:2.

The secondary reaction was performed by supplying a mixed gas having the same composition as that adopted in Example 6 to the secondary reaction vessel 11 filled with the reaction catalyst under the reaction conditions shown in Table 2 in the same manner as Example 6. The results obtained from this example are shown in Table 2.

EXAMPLE 15

A primary reaction was performed under the same condition as Example 1. Therefore, the composition of the resulting reactant gas from the primary reaction was equivalent to that of Example 1.

For the secondary reaction catalyst, a catalyst prepared by the coprecipitation method in the following manner was adopted. A predetermined amount of iron (III) nitrate enneahydrate and a predetermined amount of lead (II) nitrite (Pb(NO$_3$)$_2$ available from Wako Pure Chemical Industries, Ltd.) were dissolved in water, and a predetermined amount of 85 percent solution of phosphoric acid was added thereto. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of iron:lead:phosphorus was 1:0.8:2.

The secondary reaction was performed by supplying a mixed gas having the described in Example 1 composition, to the secondary reaction vessel 11 filled with the reaction catalyst under the reaction conditions shown in Table 2 in the same manner as Example 1. The results obtained from this example are shown in Table 2.

EXAMPLE 16

A primary reaction was performed under the same condition as Example 1. Therefore, the composition of the resulting reactant gas from the primary reaction was equivalent to that of Example 1.

For the secondary reaction catalyst, a catalyst prepared by the coprecipitation method in the following manner was adopted. A predetermined amount of chromium (III) nitrate enneahydrate and a predetermined amount of aluminium (III) nitrate enneahydrate were dissolved in water, and a predetermined amount of 85 percent solution of phosphoric acid was added thereto. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of chromium:aluminium:phosphorus was 1:1:2.

The secondary reaction was performed by supplying a mixed gas having the same composition as that employed in Example 3, to the secondary reaction vessel 11 filled with the reaction catalyst under the reaction conditions shown in Table 2 in the same manner as Example 3. The results obtained from this example are shown in Table 2.

EXAMPLE 17

A primary reaction was performed under the same condition as Example 1. Therefore, the composition of the resulting reactant gas from the primary reaction was equivalent to that of Example 1.

For the secondary reaction catalyst, a catalyst prepared by the coprecipitation method in the described manner was

21 adopted. A predetermined amount of aluminium (III) nitrate enneahydrate was dissolved in water, and a predetermined amount of 85 percent solution of phosphoric acid was added. To the solution, a predetermined amount of nickel phosphate heptahydrate ($Ni_3(PO_4)_2 \cdot 7H_2O$) available from Yoneyama Chemical Industries Ltd.) was added in a form of powder without having applied thereto any treatment. To the solution, 28 percent ammonium solution was further added dropwise to generate precipitate. This dropwise addition of ammonium solution was stopped when the solution showed a pH of 7. The resulting precipitate was condensed, dried and calcined and the particle diameter thereof was adjusted in the same manner as Example 2. Then, the secondary reaction vessel 11 was filled with the secondary reaction catalyst. The ratio of nickel:aluminium:phosphorus was 1.5:1:2.

The secondary reaction was performed by supplying a mixed gas having the same composition as that adopted in Example 3, to the secondary reaction vessel 11 filled with the reaction catalyst under the reaction conditions shown in Table 2 in the same manner as Example 3. The results obtained from this example are shown in Table 2.

EXAMPLE 18

A primary reaction was performed under the same condition as Example 1. Therefore, the composition of the resulting reactant gas from the primary reaction was equivalent to that of Example 1.

For the secondary reaction catalyst, silica supporting 12-molybdophosphoric acid ($H_3PMo_{12}O_{40}$) prepared in the following manner was used. As a support material for the catalyst, silica in spherical shape (CARIACT Q-50 (Fujisilysia Chemical, LTD.) adjusted to 9 to 20 mesh was used. A predetermined amount of the described silica was added to a solution of 12-molybdophosphoric acid ($H_3PMo_{12}O_{40} \cdot nH_2O$ available from Nippon Inorganic Chemical Industries, Ltd.), and was condensed in a hot bath to support 12-molybdophosphoric acid. Thereafter, it was dried in the air at 120° C. Then, the secondary reaction vessel 11 was filled with the resulting secondary reaction catalyst. In this example, the concentration of the 12-molybdophosphoric acid of 35 percent by weight based on anhydride was obtained.

In the secondary reaction, a mixed gas having the same composition as that adopted in Example 1 was supplied to the secondary reaction vessel 11 that was filled with the secondary reaction catalyst, and under reaction conditions shown in Table 2, a reaction was performed in the same manner as Example 1. The results obtained from this example are shown in Table 2.

22

EXAMPLE 19

A primary reaction was performed under the same condition as Example 8. Therefore, the composition of the resulting reactant gas from the primary reaction was equivalent to that of Example 8.

For the secondary reaction catalyst, silica support material of 11-molybdovanadophosphoric acid ($H_4PMO_{11}VO_{40}$) prepared in the following manner was used. Namely, a predetermined amount of 11-molybdovanadophosphoric acid ($H_4PMO_{11}VO_{40} \cdot nH_2O$ available from Nihon Inorganic Chemical Industries, Ltd.) was supported by a predetermined amount of silica as in the same manner as Example 18. Then, the secondary reaction vessel 11 was filled with the resulting secondary reaction catalyst. In this example, the concentration of 11-molybdovanadophosphoric acid based on anhydride of 29 percent by weight was obtained.

In the secondary reaction, a mixed gas having the same composition as that adopted in Example 1 was supplied to the secondary reaction vessel 11 filled with the secondary reaction catalyst, and under reaction conditions shown in Table 2, a reaction was performed in the same manner as Example 8. The results obtained from this example are shown in Table 2.

EXAMPLE 20

A primary reaction was performed under the same condition as Example 8. Therefore, the composition of the resulting reactant gas from the primary reaction was equivalent to that of Example 8.

For the secondary reaction catalyst, silica support material of potassium partially substituted 11-molybdovanado phosphoric acid ($KH_3PMO_{11}VO_{40}$) prepared in the following manner was used. Then, a predetermined amount of a solution of potassium carbonate ($K_2CO_3$ available from Wako Pure Chemical Industries, Ltd.) was added to a solution of 11-molybdovanado phosphoric acid to obtain a uniform solution. Thereafter, the resulting uniform solution was supported by a predetermined amount of silica in the same manner as Example 18. In this example, the concentration of potassium partially substituted 11-molybdovanado phosphoric acid of 30 percent by weight based on anhydride was obtained.

In the secondary reaction, a mixed gas having the same composition as that employed in Example 8 was supplied to the secondary reaction vessel 11 filled with the secondary reaction catalyst, and under reaction conditions shown in Table 2, a reaction was performed in the same manner as Example 8. The results obtained from this example are shown in Table 2.

TABLE 2

| EXAM-PLE | COMPOSITION OF GAS SUPPLIED (VOL %, NITROGEN BALANCE) | | | | SPACE VELOCITY SV | REACTION TEMPERATURE | CONVERSION OF GLO + GAL | SELECTIVITY OF | YIELD OF MGO (%) BASED ON |
|---|---|---|---|---|---|---|---|---|---|
| | GLO + GAL | OXYGEN | WATER | METHANOL | ($hr^{-1}$) | (°C.) | (%) | MGO (%) | EG |
| 11 | 4 | 5 | — | 20 | 4,500 | 180 | 89 | 75 | 55 |
| 12 | 4 | 5 | — | 20 | 3,000 | 300 | 94 | 71 | 55 |
| 13 | 3 | 4 | 10 | 18 | 4,300 | 180 | 91 | 52 | 38 |
| 14 | 4 | 5 | — | 25 | 3,000 | 250 | 92 | 72 | 55 |
| 15 | 4 | 5 | — | 20 | 2,000 | 230 | 88 | 68 | 50 |
| 16 | 4 | 5 | — | 15 | 3,000 | 300 | 92 | 63 | 52 |
| 17 | 4 | 5 | — | 15 | 3,000 | 330 | 89 | 65 | 48 |

TABLE 2-continued

| EXAMPLE | COMPOSITION OF GAS SUPPLIED (VOL %, NITROGEN BALANCE) | | | | SPACE VELOCITY SV ($hr^{-1}$) | REACTION TEMPERATURE (°C.) | CONVERSION OF GLO + GAL (%) | SELECTIVITY OF MGO (%) | YIELD OF MGO (%) BASED ON EG |
|---|---|---|---|---|---|---|---|---|---|
| | GLO + GAL | OXYGEN | WATER | METHANOL | | | | | |
| 18 | 4 | 5 | — | 20 | 3,000 | 200 | 90 | 53 | 40 |
| 19 | 3 | 4 | 10 | 18 | 3,000 | 200 | 93 | 57 | 43 |
| 20 | 3 | 4 | 10 | 18 | 3,000 | 280 | 87 | 65 | 46 |

EXAMPLE 21

A primary reaction was performed under the same condition as Example 1. Therefore, the composition of the resulting reactant gas from the primary reaction was equivalent to that of Example 1.

For the secondary reaction catalyst, iron phosphate adopted in Example 1 (hereinafter referred to as a catalyst (1)) and aluminum phosphate prepared in the following manner (hereinafter referred to as a catalyst (2)) were used.

First, aluminum (III) nitrate enneahydrate ($Al(NO_3)_3 \cdot 9H_2O$) available from Wako Chemical Industries, Ltd.) was dissolved in water, and a predetermined amount of 85 percent solution of phosphoric acid was added thereto. To the solution, 28 percent ammonium solution was added dropwise to generate precipitate. This dropwise addition of ammonium solution was stopped when the solution showed a pH of 7. The resulting precipitate was condensed, dried and calcined and the particle diameter thereof was adjusted in the same manner as Example 2, thereby obtaining the catalyst (2).

The secondary reaction vessel 11 was filled with the catalysts (1) and (2) so as to have such double layer structure that the catalyst (2) was placed on the entry opening side, while the catalyst (1) was placed on the discharge opening side in a ratio by volume of 1:1.

The secondary reaction was performed by supplying a mixed gas having the same composition as that employed in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 22

A primary reaction was performed under the same condition as Example 1. Therefore, the composition of the resulting reactant gas from the primary reaction was equivalent to that of Example 1.

The secondary reaction vessel 11 was filled with the catalysts (1) and (2) so as to have such double layer structure that the catalyst (2) was placed on the entry opening side, while the catalyst (1) was placed on the discharge opening side at a volume ratio of 2:1.

The secondary reaction was performed by supplying a mixed gas having the same composition as that employed in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 23

A primary reaction was performed under the same condition as Example 1. Therefore, the composition of the resulting reactant gas from the primary reaction was equivalent to that of Example 1.

The secondary reaction vessel 11 was filled with the catalyst (2) and chromium phosphate adopted in Example 7 (hereinafter referred to as a catalyst (3)) so as to have such double layer structure that the catalyst (2) was placed on the entry opening side, while the catalyst (3) was placed on the discharge opening side in a ratio by volume of 1:1.

The secondary reaction was performed by supplying a mixed gas having the same composition as that employed in Example 6 to the secondary reaction vessel 11 filled with the secondary reaction catalyst, and under reaction conditions shown in Table 3, a reaction was performed in the same manner as Example 6. The results obtained from this example are shown in Table 3.

EXAMPLE 24

A primary reaction was performed under the same condition as Example 1. Therefore, the composition of the resulting reactant gas from the primary reaction was equivalent to that of Example 1.

The secondary reaction vessel 11 was filled with the catalyst (2) and nickel phosphate adopted in Example 8 (hereinafter referred to as a catalyst (4)) so as to have such double layer structure that the catalyst (2) was placed on the entry opening side, while the catalyst (4) was placed on the discharge opening side at a volume ratio of 1:2.

The secondary reaction was performed by supplying a mixed gas having the same composition as that adopted in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 25

A primary reaction was performed under the same condition as Example 1. Therefore, the composition of the resulting reactant gas from the primary reaction was equivalent to that of Example 1.

The secondary reaction vessel 11 was filled with a mixture of the catalyst (1) and the catalyst (2) in a ratio by volume of 1:1.

The secondary reaction was performed by supplying a mixed gas having the same composition as that employed in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 26

A primary reaction was performed under the same condition as Example 1. Therefore, the composition of the

25 resulting reactant gas from the primary reaction was equivalent to that of Example 1.

The secondary reaction vessel 11 was filled with a mixture of the catalyst (1) and the catalyst (2) in a ratio by volume of 1:2.5.

The secondary reaction was performed by supplying a mixed gas having the same composition as that employed in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 27

A primary reaction was performed under the same condition as Example 1. Therefore, the composition of the resulting reactant gas from the primary reaction was equivalent to that of Example 1.

The secondary reaction vessel 11 was filled with a mixture of the catalyst (2) and the catalyst (3) at a volume ratio of 1:1.

The secondary reaction was performed by supplying a mixed gas having the same composition as that employed in Example 1 to the secondary reaction vessel 11 filled with the secondary reaction catalyst, and under reaction conditions shown in Table 3, a reaction was performed in the same manner as Example 1. The results obtained from this example are shown in Table 3.

EXAMPLE 28

A primary reaction was performed under the same condition as Example 1. Therefore, the composition of the resulting reactant gas from the primary reaction was equivalent to that of Example 1.

The secondary reaction vessel 11 was filled with a mixture of the catalyst (2) and the catalyst (4) in a ratio by volume of 1:1.5.

The secondary reaction was performed by supplying a mixed gas having the same composition as that employed in Example 3 to the secondary reaction vessel 11 filled with the secondary reaction catalyst, and under reaction conditions shown in Table 3, a reaction was performed in the same manner as Example 3. The results obtained from this example are shown in Table 3.

26 can be manufactured from 1,2-diol (ethylene glycol) as a raw material at high reaction efficiency (yield). For the inorganic oxide containing phosphorus, metal phosphate of various kinds (Examples 1–17) may be used alone or in combination (Examples 21–28). Additionally, it is permitted to use heteropolyacid containing phosphorus of various kinds (Examples 18–20).

In the case of adopting metal phosphate alone, glyoxylate can be manufactured at especially high yield (59%) based on ethylene glycol by adopting iron phosphate (Example 1) in a ratio of phosphorus to iron of 1 to 1. On the other hand, when more than two kinds of metal phosphate are used in combination, by filling in the secondary reaction vessel 11 aluminum phosphate on the entry opening side, and iron phosphate on the discharge opening side so as to form a double layer structure in a ratio by volume of 1:1 (example 21), glyoxylate can be manufactured from ethylene glycol especially at high yield (60 percent).

EXAMPLE 29

A primary reaction was performed using the same composition of the supplied gas as Example 1 under the same conditions as Example 1. Therefore, the composition of the resulting reactant gas from the primary reaction was equivalent to that of Example 1.

The secondary reaction was performed by supplying the mixed gas of the same composition except that ethanol was adopted in place of methanol of Example 1 using the secondary reaction vessel 11 that was filled with the catalyst (1) in the same manner as Example 1 under the conditions shown in Table 4. The results obtained from this Example are shown in Table 4. For comparison, the conditions and results of Example 1 and Example 7 are also shown in Table 4.

EXAMPLE 30

A primary reaction was performed using the same composition of the supplied gas as Example 1 under the same conditions as Example 1. Therefore, the composition of the resulting reactant gas from the primary reaction was equivalent to that of Example 1.

The secondary reaction was performed by supplying the same composition of the mixed gas, except that ethylene was adopted, using the secondary reaction vessel 11 that was

TABLE 3

| EXAM-PLE | COMPOSITION OF GAS SUPPLIED (VOL %, NITROGEN BALANCE) | | | | SPACE VELOCITY SV ($hr^{-1}$) | REACTION TEMPERATURE (°C.) | CONVERSION OF GLO + GAL (%) | SELECTIVITY OF MGO (%) | YIELD OF MGO (%) BASED ON EG |
|---|---|---|---|---|---|---|---|---|---|
| | GLO + GAL | OXYGEN | WATER | METHANOL | | | | | |
| 21 | 4 | 5 | — | 20 | 3,000 | 250 | 100 | 78 | 65 |
| 22 | 4 | 5 | — | 20 | 3,000 | 280 | 98 | 74 | 60 |
| 23 | 4 | 5 | — | 25 | 3,000 | 280 | 95 | 69 | 54 |
| 24 | 4 | 5 | — | 20 | 3,000 | 300 | 96 | 67 | 53 |
| 25 | 4 | 5 | — | 20 | 3,000 | 280 | 100 | 70 | 58 |
| 26 | 4 | 5 | — | 20 | 4,000 | 240 | 97 | 66 | 53 |
| 27 | 4 | 5 | — | 20 | 3,000 | 260 | 96 | 68 | 54 |
| 28 | 4 | 5 | — | 15 | 3,000 | 350 | 95 | 62 | 49 |

As is evident from the described examples 1 through 28, by adopting an inorganic oxide containing phosphorus as a secondary reaction catalyst, α-oxocarboxylate (glyoxylate) filled with the catalyst (1) in the same manner as Example 1 under the conditions shown in Table 4. The results obtained from this Example are shown in Table 4.

EXAMPLE 31

A primary reaction was performed using the same composition of the supplied gas as Example 7 under the same condition as Example 7. Therefore, the composition of the resulting reactant gas from the primary reaction was equivalent to that of Example 1.

The secondary reaction was performed by supplying the same composition of the mixed gas, except that propanol was adopted, using the secondary reaction vessel 11 that was filled with the catalyst (3) in the same manner as Example 7 under the conditions shown in Table 4. The results obtained from this Example are shown in Table 4.

EXAMPLE 32

A primary reaction was performed in the same manner as Example 1 except that the composition of the supplied gas was altered so as to have EG of 7 vol. percent, and oxygen of 6 vol. percent (nitrogen balance). As a result, a conversion of EG of 91 percent, a yield of GLO of 54 percent and a yield of GAL of 20 percent were obtained as shown in Table 5. For comparison, the reaction conditions for Example 1 and Example 7 and the results thereof are shown in Table 5.

To the secondary reaction 11, a gas obtained from the secondary reaction was supplied, and a pure oxygen was supplied to make up for the insufficient amount of oxygen. Furthermore, gaseous methanol was supplied so as to have a composition of the supplied gas of a sum of GLO and GAL of 4 vol. percent, oxygen of 5 vol. percent and methanol of 20 vol. percent (nitrogen balance) as shown in Table 6.

The secondary reaction was performed by supplying a mixed gas of the described composition using the secondary reaction vessel that was filled with the catalyst (1) in the same manner as Example 1 under reaction conditions shown in Table 6. The results obtained from this example are shown in Table 6. For comparison, reaction conditions and results of Example 1 and Example 7 are shown in Table 6.

The yield of RGO based on the total amount of GLO and GAL shown in Table 6 was obtained from the following equation:

The yield of RGO (%) based on the total amount of GLO and GAL=(RGO (mol) produced/the total amount (mol) of GLO and GAL resulting from the primary reaction)×100.

EXAMPLE 33

A secondary reaction was performed using the same composition of the supplied gas as Example 32 under the same conditions as Example 32. Therefore, the composition of the resulting reactant gas from the primary reaction was equivalent to that of Example 32.

A secondary reaction was performed by supplying the same composition of the mixed gas as Example 32 to the secondary reaction vessel 11 that was filled with the catalyst (3) under the same reaction conditions shown in Table 6 in the same manner as Example 31. The results obtained from this example are shown in Table 6.

EXAMPLE 34

A secondary reaction was performed using gaseous α-oxoaldehyde obtained by heating a solution of

TABLE 4

| EXAMPLE | COMPOSITION OF GAS SUPPLIED (VOL %, NITROGEN BALANCE) | | | | SPACE VELOCITY SV (hr⁻¹) | REACTION TEMPERATURE (°C.) | CONVERSION OF GLO + GAL (%) | SELECTIVITY OF RGO (%) | YIELD OF RGO (%) BASED ON EG |
|---|---|---|---|---|---|---|---|---|---|
| | GLO + GAL | OXYGEN | ALCOHOL OR OLEFIN | | | | | | |
| 1 | 4 | 5 | METHANOL | 20 | 2,000 | 250 | 100 | 74 | 61 |
| 7 | 4 | 5 | METHANOL | 20 | 2,000 | 250 | 91 | 65 | 49 |
| 29 | 4 | 5 | ETHANOL | 20 | 3,000 | 250 | 98 | 69 | 56 |
| 30 | 4 | 5 | ETHYLENE | 20 | 3,000 | 280 | 92 | 56 | 43 |
| 31 | 4 | 5 | PROPANOL | 20 | 3,000 | 250 | 87 | 64 | 46 |

In table 4, RGO is an ester of glyoxylic acid.

As is evident from Example 1, Examples 29–31, in the case of adopting methanol, ethanol, and propanol as alcohol, and the case of adopting ethylene as olefin, α-oxocarboxylate can be manufactured efficiently (at high yield).

α-oxoaldehyde in place of gaseous α-oxoaldehyde (2) and α-hydroxyaldehyde (3) resulting from the primary reaction.

For a solution of α-oxoaldehyde, 40 percent aqueous solution of glyoxal (available from Wako Pure Chemical Industries, Ltd.) was used. A raw material was supplied in the following manner. A solution obtained by mixing an aqueous solution of glyoxal and a predetermined amount of methanol was placed in the raw material tank 12, and was supplied to the vaporizing chamber 14 for feeding the mixed solution, thereby obtaining a mixed gas as a raw material.

To the secondary reaction vessel 11, a mixed gas was supplied as well as air and nitrogen so that the supplied gas has a composition of 5 vol. percent of GLO, 4 vol. percent of oxygen, 19 vol. percent of water and 20 vol. percent of methanol (nitrogen balance).

The secondary reaction was performed by supplying the mixed gas of the described composition using the secondary reaction vessel 11 which was filled with the catalyst (1) under conditions shown in Table 6 in the same manner as Example 1. The results obtained from this example are shown in Table 6.

EXAMPLE 35

A secondary reaction was performed using gaseous α-hydroxyaldehyde obtained by heating a solution of α-hydroxyaldehyde in place of gaseous α-oxoaldehyde (2) and α-hydroxyaldehyde (3) resulting from the primary reaction.

For a solution of α-hydroxyaldehyde, a solution of glycolaldehyde obtained by dissolving a commercially available dimer of glycolaldehyde (available from Wako Pure Chemical Industries, Ltd.) in water and methanol was used. A raw material was supplied in the following manner. A solution obtained by mixing a solution of glycolaldehyde and a predetermined amount of methanol was placed in the raw material tank 12, and was supplied to the vaporizing chamber 14 for feeding the mixed solution, thereby obtaining a mixed gas as a raw material.

To the secondary reaction vessel 11, a mixed gas was supplied as well as air and nitrogen so that the supplied gas had a composition of 5 vol. percent of GAL, 4 vol. percent of oxygen, 19 vol. percent of water and 20 vol. percent of methanol (nitrogen balance).

The secondary reaction was performed by supplying the mixed gas of the described composition using the secondary reaction vessel 11 which was filled with the catalyst (1) under conditions shown in Table 6 in the same manner as Example 1. The results obtained from this example are shown in Table 6.

TABLE 5

| EXAMPLE | COMPOSITION OF GAS SUPPLIED (VOL %, NITROGEN BALANCE) | | CONVERSION OF EG (%) | YIELD OF GLO (%) | YIELD OF GAL (%) |
| --- | --- | --- | --- | --- | --- |
|  | EG | OXYGEN |  |  |  |
| 1 | 6 | 7 | 98 | 82 | 1 |
| 7 | 6 | 7 | 98 | 82 | 1 |
| 32 | 7 | 6 | 91 | 54 | 20 |
| 33 | 7 | 3 | 91 | 54 | 20 |

(III) phosphate tetra-hydrate ($FePO_4 \cdot 4H_2O$ available from Katayama Chemical Industries Ltd.) and a predetermined amount of silica ($SiO_2$ available from Mizusawa Chemical Co. Ltd. "Mizukasil P-802") were well mixed in a mortar, and a moisture thereof was adjusted with water. Thereafter, the resulting mixture was dried, calcined and the diameter of the particles were adjusted in the same manner as Example 1. A ratio of phosphorus to iron in the resulting catalyst for secondary reaction was 1 to 1. Silica was added so that a content thereof becomes 20 percent with respect to a total amount of the secondary reaction catalyst.

Then, the secondary reaction was performed by supplying a mixed gas having the same composition as Example 1 to the secondary reaction vessel 11 that was filled with the described catalyst for secondary reaction in the same manner as Example 1 under conditions shown in Table 7. The results obtained from this example are shown in Table 7.

EXAMPLE 37

A primary reaction was performed under the same condition as Example 1. Therefore, a composition of a reactant gas for the primary reaction was the same as Example 1.

As a secondary reaction catalyst, titania added iron (III) phosphate prepared in the following manner was adopted.

TABLE 6

| EXAMPLE | COMPOSITION OF GAS SUPPLIED (VOL %, NITROGEN BALANCE) | | | | SPACE VELOCITY SV ($hr^{-1}$) | REACTION TEMPERATURE (°C.) | CONVERSION OF GLO + GAL (%) | SELECTIVITY OF MGO (%) | YIELD OF MGO BASED ON EG | YIELD OF MGO BASED ON GLO + GAL |
| --- | --- | --- | --- | --- | --- | --- | --- | --- | --- | --- |
|  | GLO | GAL | OXYGEN | WATER | METHANOL |  |  |  |  |  |
| 1 | 3.9 | 0.1 | 5 | — | 20 | 2,000 | 250 | 100 | 74 | 61 | 74 |
| 6 | 3.9 | 0.1 | 5 | — | 20 | 2,000 | 250 | 91 | 65 | 49 | 59 |
| 32 | 2.9 | 1.1 | 5 | — | 20 | 3,000 | 250 | 90 | 72 | 52 | 71 |
| 33 | 2.9 | 1.1 | 5 | — | 20 | 3,000 | 280 | 93 | 62 | 43 | 58 |
| 34 | 5.0 | — | 4 | 19 | 20 | 3,000 | 280 | 97 | 62 | — | 60 |
| 35 | — | 5.0 | 4 | 14 | 20 | 3,000 | 280 | 92 | 60 | — | 55 |

As is evident from a comparison between Example 1 and Example 32 and a comparison between Example 7 and Example 33, glyoxylate can be manufactured efficiently (yield) irrespectively of a ratio of α-oxoaldehyde (2) to α-hydroxyaldehyde (3) in a mixed gas to be adopted as a raw material of the secondary reaction.

As is evident from Example 34, glyoxylate can be manufactured efficiently (at high yield) by a vapor phase oxidization by molecular oxygen in the presence of an inorganic oxide catalyst containing phosphorus by adopting a solution of α-oxoaldehyde as a raw material and adding thereto gaseous alcohol.

As is evident from Example 35, glyoxylate can be manufactured efficiently (at high yield) by a vapor phase oxidization with molecular oxygen in the presence of an inorganic oxide catalyst containing phosphorus by adopting a solution of α-hydroxyaldehyde as a raw material and adding thereto gaseous alcohol.

EXAMPLE 36

A primary reaction was performed under the same condition as Example 1. Therefore, a composition of a reactant gas for the primary reaction was the same as Example 1.

As a catalyst for the secondary reaction, silica added iron (III) phosphate prepared in the following manner was adopted. Namely, a predetermined amount of reagent of iron (III) phosphate tetra-hydrate ($FePO_4 \cdot 4H_2O$ available from Katayama Chemical Industries Ltd.) and a predetermined amount of reagent of anatase-type titanium dioxide ($TiO_2$ available from Wako Pure Chemical Industries, Ltd.) were well mixed in the mortar, and a moisture thereof was adjusted with water. Thereafter, the resulting mixture was dried, calcined and the diameter of the particles were adjusted in the same manner as Example 1. A ratio of phosphorus to iron in the resulting catalyst for secondary reaction was 1 to 1. An amount of titania added was selected to be 30 percent with respect to a total amount of the secondary reaction catalyst.

The secondary reaction was performed by supplying a mixed gas having the same composition as that adopted in Example 1 to the secondary reaction vessel 11 filled with the reaction catalyst under the reaction conditions shown in Table 7 in the same manner as Example 1. The results obtained from this example are shown in Table 7.

EXAMPLE 38

A primary reaction was performed under the same condition as Example 1. Therefore, a composition of a reactant gas for the primary reaction was the same as Example 1.

As a secondary reaction catalyst, titania added iron phosphate prepared in the following manner was adopted.

Specifically, a predetermined amount of iron (III) nitrate enneahydrate (Fe(NO$_3$)$_3$·9H$_2$O available from Wako Pure Chemical Industries, Ltd.) was dissolved in water, and a predetermined amount of 85 percent solution of phosphoric acid (H$_3$PO$_4$ available from Wako Pure Chemical Industries, Ltd.) was added thereto. While stirring the solution, a predetermined amount of anatase-type titanium dioxide (TiO$_2$ available from Wako Pure Chemical Industries, Ltd.) was added. To the solution, 28 percent ammonium solution (available from Kishida Chemical Co., Ltd.) was added dropwise to generate precipitate. This dropwise addition of the ammonium solution was stopped when the solution showed a pH of 7. The resulting precipitate was condensed into a slurry form in a hot bath, and the resulting slurry was dried and calcined and the particle diameter thereof was adjusted in the same manner as Example 1. Then, the secondary reaction vessel 11 was filled with the secondary reaction catalyst. The ratio of phosphorus to iron was 1.2 to 1. The amount of titania added was selected to be 30 percent with respect to the total amount of the secondary catalyst.

The gas supplied in the secondary reaction was obtained by adding pure oxygen and gaseous methanol to the reactant gas resulting from the primary reaction so as to have the composition of total amount of GLO and GAL of 4 vol. percent, oxygen of 5 vol. percent and methanol of 10 vol. percent (nitrogen balance) as shown in Table 7.

The secondary reaction was performed by supplying the mixed gas having the same composition as that adopted in Example 1 to the secondary reaction vessel 11 filled with the reaction catalyst under the reaction conditions shown in Table 7 in the same manner as Example 1. The results obtained from this example are shown in Table 7.

EXAMPLE 39

A primary reaction was performed under the same condition as Example 1. Therefore, a composition of a reactant gas for the primary reaction was the same as Example 1.

As a catalyst for secondary reaction, zirconia added chromium phosphate prepared in the following manner was adopted. Namely, a predetermined amount of reagent of chromium (III) nitrate enneahydrate (Cr(NO$_3$)$_3$·9H$_2$O available from Wako Pure Chemical Industries, Ltd.) was dissolved in water, and a predetermined amount of 85 percent solution of phosphoric acid was added to obtain a uniform solution. To the solution, a reagent of zirconium oxide (ZrO$_2$ available from Mitsuwa Chemical Ltd.) was added dropwise, and this dropwise addition of 28 percent ammonium solution was continued until the solution showed a pH of 7 to generate precipitate. The resulting precipitate was condensed, dried and calcined and the particle diameter thereof was adjusted in the same manner as Example 2. The ratio of phosphorus to chrome in the catalyst for secondary reaction was 1 to 1. Zirconia was added so that a content thereof becomes 20 percent with respect to a total amount of the catalyst for the secondary reaction, i.e., a total amount of chrome phosphate and zirconia.

Then, the secondary reaction was performed by supplying a mixed gas having the same composition as Example 1 to the secondary reaction vessel 11 that was filled with the described catalyst for secondary reaction in the same manner as Example 1 under conditions shown in Table 7. The results obtained from this example are shown in Table 7.

EXAMPLE 40

A primary reaction was performed under the same condition as Example 1. Therefore, a composition of a reactant gas for the primary reaction was the same as Example 1.

As a catalyst for secondary reaction, a catalyst prepared in the following manner was adopted. Namely, a predetermined amount of iron (III) nitrate enneahydrate was dissolved in water, and a predetermined amount of 85% solution of phosphoric acid was added thereto. Furthermore, a solution obtained by dissolving a predetermined amount of ammonium vanadate (NH$_4$VO$_3$ available from Kishida Chemical Co., Ltd. was added beforehand to a solution of oxalic acid ((COOH)$_2$ available from Wako Pure Chemical Industries, Ltd.) as a V source. Then, a reagent of niobium oxide (Nb$_2$O$_5$ available from Wako Pure Chemical Industries, Ltd.) was added. Further, 28 percent ammonium solution was added dropwise so as to have a pH of 7 to generate precipitate. The resulting precipitate was condensed, dried and calcined and the particle diameter thereof was adjusted in the same manner as Example 2. The ratio of iron:vanadium:phosphorus in the catalyst for secondary reaction was 1:0.2:1. Niobium oxide was added so that a content thereof became 20 percent with respect to a total amount of the secondary reaction catalyst, i.e., a total amount of iron phosphate including vanadium, and niobium oxide.

Then, the secondary reaction was performed by supplying a mixed gas having the same composition as Example 1 to the secondary reaction vessel 11 that was filled with the described catalyst for secondary reaction in the same manner as Example 1 under conditions shown in Table 7. The results obtained from this example are shown in Table 7.

TABLE 7

| EXAMPLE | COMPOSITION OF GAS SUPPLIED (VOL %, NITROGEN BALANCE) | | | | SPACE VELOCITY SV (hr$^{-1}$) | REACTION TEMPERATURE (°C.) | CONVERSION OF GLO + GAL (%) | SELECTIVITY OF MGO (%) | YIELD OF MGO (%) BASED ON EG |
|---|---|---|---|---|---|---|---|---|---|
| | GLO + GAL | OXYGEN | WATER | METHANOL | | | | | |
| 36 | 4 | 5 | — | 20 | 2,000 | 260 | 100 | 76 | 62 |
| 37 | 4 | 5 | — | 20 | 2,000 | 250 | 99 | 78 | 63 |
| 38 | 4 | 5 | — | 10 | 3,000 | 270 | 95 | 69 | 54 |
| 39 | 4 | 5 | — | 20 | 2,000 | 240 | 99 | 63 | 52 |
| 40 | 4 | 5 | — | 20 | 3,000 | 200 | 92 | 77 | 58 |

EXAMPLE 41

A primary reaction for obtaining gaseous pyruvic aldehyde (PAL) and lactic aldehyde (2-hydroxypropanal) by oxidative dehydrogenation of propyleneglycol (hereinafter referred to as PG) was performed using the aforementioned reaction vessel in accordance with a reaction using EG as a raw material under the following conditions. Namely, the vaporizing chamber 3 was heated beforehand and was maintained at 180° C. The triethyl phosphite was added in an amount with respect to the PG in the primary reaction raw material such that the concentration of phosphorus with respect to PG becomes 60 ppm.

A mixed gas to be supplied to the primary reaction vessel 7 from the vaporization chamber 3, i.e., the composition of the gas to be applied to the primary reaction vessel 7 was selected to have PG of 4 vol. percent, and oxygen of 7 vol. percent (nitrogen balance) as shown in Table 8. As a catalyst for use in the primary reaction, 0.8 g of metallic silver of a particle diameter of 20 to 30 mesh (available from Yokohama Metal Co., Ltd.) was adopted. The primary reaction was performed under the conditions of a reaction temperature of 550° C. and a space velocity (SV) of 830,000 $hr_{-1}$.

After the primary reaction was performed under the above-mentioned conditions, a reactant gas was analyzed by a method to be described later. As a result, the reactant gas had a PG conversion of 100 percent and a yield of PAL of 80 percent, and lactic aldehyde (2-hydroxypropanal) was produced in a small amount as shown in Table 8.

The secondary reaction for obtaining methyl pyruvate was performed using the above-mentioned reaction vessel under the following conditions. Namely, methanol was adopted as alcohol, and the gas composition to be supplied from the vaporizing chamber 14 to the secondary reaction vessel 11 was selected to have PAL of 4 vol. percent, oxygen of 5 vol. percent and methanol of 20 vol. percent (nitrogen balance). Additionally, pure oxygen was applied through a gas supply opening 10 to ensure a sufficient amount of oxygen.

As a catalyst for the secondary reaction, iron phosphate adopted in Example 1 was adopted. The secondary reaction vessel 11 was filled with the catalyst for the secondary reaction. The secondary reaction was performed by supplying a mixed gas of the described composition to the secondary reaction vessel 11 that was filled with the catalyst for the secondary reaction under the conditions shown in Table 9. The results obtained from this example are also shown in Table 9.

In Example 40 and Example 41, the conversion, selectivity and yield were calculated in the following manner. First, a reactant gas of the secondary reaction was analyzed using the analysis method described in Example 1. Then, unreacted propylene glycol and pyruvic aldehyde were determined. The reactant gas resulting from the secondary reaction was also analyzed, and unreacted pyruvic aldehyde using the described analysis method.

The reacted PG (mol)=PG supplied (mol)-unreacted PG (mol)

The conversion of PG (%)=(reacted PG (mol)/PG Supplied) (mol)×100

The yield of PAL (%)=(PAL generated from the primary reaction (mol)/PG supplied (mol))×100

The reacted PAL (mol)=PAL (mol) resulting from the primary reaction-unreacted PAL (mol)

The conversion of Pa (%)=(reacted PAL (mol)/PAL(mol) resulting from the primary reaction (mol))×100

The yield of methyl pyruvate (%)=(generated methyl pyruvate (mol)/reacted PAL (mol))×100

The yield of methyl pyruvate (%) based on PG=(generated methyl pyruvate (mol)/PG supplied (mol))×100.

EXAMPLE 42

A primary reaction was performed under the same condition as Example 41 as shown in Table 8. Therefore, a composition of a reactant gas for the primary reaction was the same as Example 41. As a catalyst for the secondary reaction, nickel phosphate adopted in Example 7 was adopted, and the mixed gas of the same composition as Example 41 was supplied to the secondary reaction vessel 11 that was filled with the secondary reaction catalyst, and the secondary reaction was performed under the conditions shown in Table 9 in the same manner as Example 41. The results obtained from this example 41 are shown in Table 9.

TABLE 8

| EXAMPLE | COMPOSITION OF GAS SUPPLIED (VOL. %, NITROGEN BALANCE) | | CONVERSION OF PG (%) | YIELD OF PYRUVIC ALDEHYDE (%) |
|---|---|---|---|---|
| | PG | OXYGEN | | |
| 41 | 4 | 7 | 100 | 80 |
| 42 | 4 | 7 | 100 | 80 |

PG is propylene glycol

TABLE 9

| EXAMPLE | COMPOSITION OF GAS SUPPLIED (VOL %, NITROGEN BALANCE) | | | SPACE VELOCITY SV ($hr^{-1}$) | REACTION TEMPERATURE (°C.) | CONVERSION OF PYRUVIC ALDEHYDE (%) | SELECTIVITY OF METHYL PYRUVATE (%) | YIELD OF METHYL PYRUVATE (%) BASED ON PG |
|---|---|---|---|---|---|---|---|---|
| | PYRUVIC ALDEHYDE | OXYGEN | METHANOL | | | | | |
| 41 | 4 | 5 | 20 | 3,000 | 270 | 88 | 58 | 41 |
| 42 | 4 | 5 | 15 | 2,500 | 320 | 81 | 49 | 32 |

As is evident from the results of Example 41 and Example 42, even when adopting propylene glycol as a raw material, α-oxocarboxylate (pyruvate) can be manufactured efficiently (high yield).

The following show the cases where only a primary reaction was performed as reference examples.

REFERENCE EXAMPLE 1

A primary reaction was performed in the same manner as Example 1 except that triethyl phosphite was added in such an amount that a concentration of phosphorus with respect to ethylene glycol is not more than 5 ppm. The main conditions adopted in this reference example are shown in Table 10. For comparison, the conditions and results of Example 1 are shown together in Table 10.

REFERENCE EXAMPLE 2

A primary reaction was performed in the same manner as Example 1 except that triethyl phosphite was added in such an amount that a concentration of phosphorus with respect to ethylene glycol is not more than 20 ppm. The main conditions adopted in this reference example are shown in Table 10.

REFERENCE EXAMPLE 3

A primary reaction was performed in the same manner as Example 1 except that triethyl phosphite was added in such an amount that a concentration of phosphorus with respect to ethylene glycol is not more than 40 ppm. The main conditions adopted in this reference example are shown in Table 10.

REFERENCE EXAMPLE 4

A primary reaction was performed in the same manner as Example 1 except that triethyl phosphite was added in such an amount that a concentration of phosphorus with respect to ethylene glycol is not more than 80 ppm. The main conditions adopted in this reference example are shown in Table 10.

TABLE 10

| | CONCENTRATION OF PHOSPHORUS WITH RESPECT TO EG (ppm) | GLO YIELD (%) | GAL YIELD (%) |
|---|---|---|---|
| REFERENCE EXAMPLE 1 | 5 OR LESS | 43 | 10 |
| REFERENCE EXAMPLE 2 | 20 | 60 | 10 |
| REFERENCE EXAMPLE 3 | 40 | 71 | 6 |
| EXAMPLE 1 | 60 | 82 | 1 |
| REFERENCE EXAMPLE 4 | 80 | 64 | 8 |

As is evident from the results shown in Table 10, by selecting an amount of triethyl phosphite such that a concentration of ethylene glycol is not less than 20 ppm, the total yield of α-oxoaldehyde (2) and α-hydroxyaldehyde (3) resulting from the primary reaction can be improved. For the reaction condition of Example 1, it is the most preferable to add phosphorus in an amount of 60 ppm with respect to ethylene glycol under conditions of Example 1. In contrast, both in the case where an amount of triethyl phosphite is reduced as in reference examples 1 through 3, and in the case where triethyl phosphite is increased as in reference example 4, the yield of the sum of α-oxoaldehyde (2) and α-hydroxyaldehyde (3) is lowered as is evident from reference examples 1 through 3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of manufacturing α-oxocarboxylate, comprising the step of:
   carrying out a vapor phase oxidation of α-oxoaldehyde and/or α-hydroxyaldehyde and alcohol or olefin in the presence of oxygen and a catalyst.

2. The method as set forth in claim 1, wherein:
   said α-oxoaldehyde is glyoxal, and said α-hydroxyaldehyde is glycol aldehyde.

3. The method as set forth in claim 1, further comprising the step of:

producing gaseous α-oxoaldehyde of formula (2) and/or α-hydroxyaldehyde of formula (3) obtained by carrying out a vapor phase oxidation of 1,2-diol of formula (1) prior to carrying out the vapor phase oxidation of α-oxoaldehyde and/or α-hydroxyaldehyde and alcohol or olefin.

(R is a hydrogen atom or an organic residue),

(R is a hydrogen atom or an organic residue),

(R is a hydrogen atom or an organic residue).

4. The method recited in claim 3, wherein:
   said 1,2-diol has a substituent represented by R in formula (1) of at least one kind selected from the group consisting of a hydrogen atom, a saturated hydrocarbon group with 1 to 4 carbon atoms, an unsaturated aliphatic hydrocarbon group with 2 to 3 carbon atoms, and an aromatic aliphatic hydrocarbon group.

5. The method as set forth in claim 3, wherein:
   said 1,2-diol is ethylene glycol.

6. The method as set forth in claim 3, wherein:
   said 1,2-diol is propylene glycol.

7. The method as set forth in claim 3, wherein:
   said step of the vapor phase oxidation of 1,2-diol is carried out at reaction temperature in a range of from 400° to 600° C.

8. The method as set forth in claim 7, wherein
   said step of the vapor phase oxidation of 1,2-diol is carried out by feeding a mixed gas obtained after mixing oxygen with 1,2-diol in a catalyst layer made of a metallic silver.

9. The method as set forth in claim 8, wherein a ratio by volume in a composition of 1,2-diol to oxygen of said mixed gas is in a range of from 4/10 to 10/4 (volumetric ratio).

10. The method as set forth in claim 8, wherein:
    said mixed gas is fed in the first catalyst layer at a space velocity (SV) in a range of from 10,000 to 1,000,000 hr$^{-1}$.

11. The method as set forth in claim 3, wherein:
    said step of the vapor phase oxidation of 1,2-diol is carried out in the presence of metallic silver.

12. The method as set forth in claim 11, further comprising the step of:
    adding a component containing phosphorus to said 1,2-diol prior to performing the vapor phase oxidation of 1,2-diol.

13. The method as set forth in claim 12, wherein:
    said component containing phosphorus is added in such an amount that a concentration of phosphorus with respect to said 1,2-diol is not less than 20 ppm.

14. The method as set forth in claim 12, wherein:
    said component containing phosphorus is added in such an amount that a concentration of phosphorus with respect to said 1,2-diol is in a range of from 40 to 100 ppm.

15. The method as set forth in claim 12, wherein:

said component containing phosphorus is added in such an amount that a concentration of phosphorus with respect to said 1,2-diol is in a range of from 50 to 70 ppm.

16. The method as set forth in claim 1, further comprising:

a step of generating α-oxoaldehyde and/or α-hydroxyaldehyde by heating a solution of α-oxoaldehyde and/or a solution of α-hydroxyaldehyde prior to carrying out the vapor phase oxidation of α-oxoaldehyde and/or α-hydroxyaldehyde and alcohol or olefin.

17. The method as set forth in claim 1, wherein:

said alcohol is an alcohol of at least one kind selected from the group consisting of alkyl alcohol with 1 to 18 carbon atoms and aromatic alcohol.

18. The method as set forth in claim 1, wherein:

said alcohol is alkyl alcohol with 1 to 4 carbon atoms.

19. The method as set forth in claim 1, wherein:

said alcohol is methanol.

20. The method as set forth in claim 1, wherein:

said olefin has 2 to 4 carbon atoms.

21. The method as set forth in claim 1, wherein:

a volumetric ratio of a total volume of α-oxoaldehyde and α-hydroxyaldehyde/oxygen/alcohol or olefin in a composition of said mixed gas is 3~5/3~8/10~25.

22. The method as set forth in claim 1, wherein:

said step of carrying out a vapor phase oxidation of α-oxoaldehyde and/or α-hydroxyaldehyde and alcohol or olefin includes a step of feeding a resulting mixed gas in said catalyst layer composed of the catalyst.

23. The method as set forth in claim 22, wherein:

said mixed gas is fed in a catalyst layer at a space velocity (SV) in a range of from 500 to 10,000 $hr^{-1}$.

24. The method as set forth in claim 1, wherein:

the vapor phase oxidation of α-oxoaldehyde and/or α-hydroxyaldehyde and alcohol or olefin is carried out at reaction temperature in a range of from 150° to 500° C.

25. The method as set forth in claim 1, wherein:

the catalyst includes an inorganic oxide containing phosphorus.

26. The method as set forth in claim 25, wherein:

said inorganic oxide containing phosphorus is composed of metal phosphate.

27. The method as set forth in claim 26, wherein:

a ratio of metal/phosphorus in said metal phosphate is in a range of from 1/2 to 1/0.5.

28. The method as set forth in claim 26, wherein:

said metal phosphate contains iron phosphate.

29. The method as set forth in claim 26, wherein:

said metal phosphate is mixed in inorganic oxide.

30. The method as set forth in claim 29, wherein:

said inorganic oxide is at least one kind selected from the group consisting of silica, titania, zirconia, niobium oxide, and diatomaceous earth.

31. The method as set forth in claim 29, wherein:

said inorganic oxide is titania.

32. The method as set forth in claim 25, wherein:

said inorganic oxide containing phosphorus is composed of heteropolyacid containing phosphorus.

33. The method as set forth in claim 32, wherein:

said inorganic oxide containing phosphorus is supported by a support material.

34. The method as set forth in claim 33, wherein:

said support material is at least one kind selected from the group consisting of silica, titania, and diatomaceous earth.

35. The method as set forth in claim 33, wherein:

said support material is silica.

* * * * *